United States Patent
Quer et al.

(10) Patent No.: US 10,202,659 B2
(45) Date of Patent: Feb. 12, 2019

(54) PRIMERS AND METHODS FOR DETECTING HUMAN HEPATITIS C VIRUS (HCV) VARIANTS IN AN ISOLATED SAMPLE

(71) Applicants: FUNDACIÓ HOSPITAL UNIVERSITARI VALL D'HEBRON—INSTITUT DE RECERCA, Barcelona (ES); CIBER (CENTRO DE INVESTIGACIÓN BIOMÉDICA EN RED), Madrid (ES); ROCHE DIAGNÒSTICS S.L., Sant Cugat del Vallès (ES)

(72) Inventors: Josep Quer, Barcelona (ES); Francisco Rodríguez, Barcelona (ES); Josep Gregori, Caldes de Montbui (ES)

(73) Assignees: Fundacio Hospital Universitari Vall D'Hebron—Institute de Recerca, Barcelona (ES); Centro de Investigacion Biomedica en Red, Madrid (ES); Roche Diagnostics S.L., Sant Cugat del Valles (ES)

( * ) Notice: Subject to any disclaimer, the term of this patent is extended or adjusted under 35 U.S.C. 154(b) by 405 days.

(21) Appl. No.: 14/392,331
(22) PCT Filed: Jul. 4, 2014
(86) PCT No.: PCT/EP2014/064281
§ 371 (c)(1),
(2) Date: Dec. 24, 2015
(87) PCT Pub. No.: WO2015/001068
PCT Pub. Date: Jan. 8, 2015

(65) Prior Publication Data
US 2016/0194726 A1 Jul. 7, 2016

(30) Foreign Application Priority Data
Jul. 5, 2013 (EP) ..................................... 13382278

(51) Int. Cl.
C12Q 1/70 (2006.01)
(52) U.S. Cl.
CPC ........ *C12Q 1/707* (2013.01); *C12Q 2600/112* (2013.01); *C12Q 2600/156* (2013.01); *C12Q 2600/16* (2013.01)
(58) Field of Classification Search
None
See application file for complete search history.

(56) References Cited

U.S. PATENT DOCUMENTS

2009/0325145 A1   12/2009   Sablon et al.

FOREIGN PATENT DOCUMENTS

WO   WO 2003/057915   7/2003
WO   WO 2008/125119   10/2008

OTHER PUBLICATIONS

Chevaliez et al. "Hepatitis C Virus (HCV) Genotype 1 Subtype Identification in New HCV Drug Development and Future Clinical Practice," PLos ONE, Dec. 2009, vol. 4, No. 12, pp. 1-9.
Hadziyannis et al. "Peginterferon-α2a and Ribavirin Combination Therapy in Chronic Hepatitis C," Annals of Internal Medicine, Mar. 2004, vol. 140, No. 5, pp. 346-357.
Kamal et al. "Peginterferon α-2b and ribavirin therapy in chronic hepatitis C genotype 4: impact of treatment duration and viral kinetics on sustained virological response," Gut, 2005, vol. 54, pp. 858-866.
Kuiken et al. "A Comprehensive System for Consistent Numbering of HCV Sequences, Proteins and Epitopes," Hepatology, 2006, vol. 44, No. 5, pp. 1355-1361.
Lauck et al. "Analysis of Hepatitis C Virus Intra-Host Diversity Across the Coding Region by Ultra-Deep Pyrosequencing," JVI Accepts published online ahead of print, J. Virol. Doi: 10.1128/JVI.06627-11, 2012, American Society for Microbiology, pp. 1-33.
Nakatani et al. "Comparative performance evaluation of hepatitis C virus genotyping based on the 5' untranslated region versus partial sequencing of the NS5B region of Brazilian patients with chronic hepatitis C," Virology Journal, Oct. 2011, vol. 8, pp. 1-5.
Park et al. "Development and clinical evaluation of a microarray for hepatitis C virus genotyping," Journal of Virological Methods, Feb. 2010, vol. 163, pp. 269-275.
Ross et al. "Genotyping of hepatitis C virus isolates by a new line probe assay using sequence information from both the 5' untranslated and the core regions," Journal of Virological Methods, Jun. 2007, vol. 143, pp. 153-160.
Sandres-Saune et al. "Determining hepatitis C genotype by analyzing the sequence of the NS5b region," Journal of Virological Methods, May 2003, vol. 109, pp. 187-193.
Sheehy et al. "A strategy for obtaining near full-length HCV cDNA clones (assemblicons) by assembly PCR," Journal of Virological Methods, Feb. 2005, vol. 123, pp. 115-124.
Simmonds et al. "Consensus Proposal for a Unified System of Nomenclature of Hepatitis C Virus Genotypes," Hepatology, Oct. 2005, vol. 42, No. 4, pp. 962-973.
Tanaka et al. "A comparison of the molecular clock of hepatitis C virus in the United States and Japan predicts that hepatocellular carcinoma incidence in the United States will increase over the next two decades," PNAS, Nov. 2002, vol. 99, No. 24, pp. 15584-15589.
Zeuzem et al. "Peginterferon alfa-2b plus ribavirin for treatment of chronic hepatitis C in previously untreated patients infected with HCV genotypes 2 or 3," Journal of Hepatology, 2004, vol. 40, pp. 993-999.
International Search Report and the Written Opinion dated Sep. 12, 2014, for PCT Application No. PCT/EP2014/064281, 16 pp.

*Primary Examiner* — Samuel C Woolwine
(74) *Attorney, Agent, or Firm* — David J. Chang

(57) ABSTRACT

The invention relates to an in vitro method for determining in an isolated sample of a subject the presence of one or more Human Hepatitis C Virus (HCV) sequence variants comprising reverse transcription and amplifying HCV RNAs molecules using specific sets of primers allowing the amplification of the HCV regions named 5'-UTR-Core and NS5B. The method includes an step for purifying the amplified regions and a sequencing step of the amplified fragments. The invention also includes specific oligonucleotides than are used as primers in the method, as well as kits including one or more of these oligonucleotides as sets of primers.

4 Claims, 4 Drawing Sheets

Specification includes a Sequence Listing.

PRIMERS AND METHODS FOR DETECTING HUMAN HEPATITIS C VIRUS (HCV) VARIANTS IN AN ISOLATED SAMPLE

The present invention is related to the field of medicine in general and specifically, to genotyping methods for diagnostics. In particular, the invention provides primers and methods for detecting and analyzing sequence variants of the human hepatitis C virus (HCV).

BACKGROUND ART

Hepatitis C is a viral infection of the liver which has also been referred to as "non A, non B hepatitis" (NANBH) until identification of the causative agent. Hepatitis C virus is one of the viruses (A, B, C, D and E), which together account for the majority of cases of viral hepatitis. Hepatitis C virus was first identified in 1989 and defined as a common cause of liver disease with an estimated 170-million infected people worldwide. Hepatitis C virus (HCV) infection affects the liver, which causes hepatitis, i. e., an inflammation of the liver. 75 to 85% of persons infected with HCV progress to chronic infection, approximately 20% of these cases develop complications of chronic hepatitis C, including cirrhosis of the liver or hepatocellular carcinoma after 20 years of infection. The current recommended treatment for HCV infections includes a combination of interferon and ribavirin drugs, with either boceprevir or telaprevir added in some cases. Overall, 50-80% of people treated are cured. Those who develop cirrhosis or liver cancer may require a liver transplant. Hepatitis C is the leading cause of liver transplantation, though the virus usually recurs after transplantation. No vaccine against hepatitis C is available.

HCV is a (+) sense single-stranded enveloped RNA virus in the Hepacivirus genus within the Flaviviridae family. The viral genome is approximately 10 kilobases (kb) in length and encodes a 3011 amino acid polyprotein precursor. The HCV genome has a large single open reading frame (ORF) coding for a unique polyprotein, said polyprotein being co- and post-translational processed by cellular and viral proteases into three structural proteins, i. e., core, E1 (envelope) and E2 (envelope) and at least seven non-structural proteins; p7 (ion channel), NS2 (protease), NS3 (serin-protease/helicase), NS4A (cofactor), NS4B (replication complex factor), NS5A (interferon resistant protein) and NS5B (RNA dependent RNA polimerase).

HCV shows a high genetic variability. The reason for this great variation is a high mutation rate and high level of viral replication through an error-prone RNA polymerase without proofreading capacity. Analysis of extensive sets of sequences from HCV isolates throughout the world has revealed the existence of six major genetic groups or genotypes, and a large number of subtypes (also named subgenotypes) within the six main genotypes. Genotypes are numbered from 1 to 6 and subtypes designated as a, b, c, etc. (i.e.: 1a, 1 b, 2a, 2b, etc.) in both cases in order of discovery. Overall sequence divergence between genotypes ranges from 31 to 34% and from 20 to 23% between subtypes An extent discussion of the adopted basis for the classification of genotypes and subtypes, as well as the standard reference methods for genotyping, can be seen in the document of Simmonds et al., "Consensus proposals for a unified system of nomenclature of hepatitis C virus genotypes", Hepatology—2005, vol. 42, pp. 963-973.

Determining the correct infection in terms of the infecting genotype (or even subtype) is fundamental in order to assign a correct treatment. Indeed, patients infected with genotypes 1 and 4 do not respond as efficiently to the standard therapy as the other genotypes, thus implying a longer therapy (48 weeks vs. 24 weeks). Or for example, genotypes 2 and 3 have great chances of response to the treatment with alfa-interferon than genotype 1. Moreover, each genotype has a different progression or development into the host. So that, genotype 1b has an accelerated development to cirrhosis than other genotypes. The genotype of an infected subject does not change during the infection history unless an additional infection takes place with another genotype or subtype.

There are several commercial kits being used for genotyping infected HCV patients, even kits that identify the subtype of a genotype. They differ in the fragment of the virus genome that is analyzed, as well as in the molecular biology tools employed in the determination of the HCV variant.

One of the methods for HCV genotyping is the Inno-Lipa HCV reverse hybridization assay (Innogenetics). In this assay, the 5'-UTR region of the virus is analyzed by reverse hybridization. Thus, non-coding 5' segments are amplified and further hybridized with reference probes that allow the genotype determination. A more robust version of Inno-Lipa is the LIPA 2.0, in which an additional region of the virus is amplified and hybridized, namely the coding core region.

Another option is the TruGene HCV 5'NC genotyping assay (Bayer). By this technique a non-coding segment of the 5' region is semi-automatically sequenced. 5'-UTR regions are amplified, sequenced and aligned with a reference sequence panel.

Also the Abbott method known as HCV genotyping ASR assay can be an option. In this case, a quantitative PCR of the 5'-UTR and NS5b regions is performed. The method proposes specific NS5b primers and probes for the detection of 1a and 1b sub-genotypes, and other 5'-UTR specific primers and probes for the genotypes and sub-genotypes 2a, 2b, 3, 4, 5 and 6.

All these methodologies appear disclosed in the document of Chevaliez S. et. al. "Hepatitis C virus (HCV) genotype 1 subtype identification in new HCV drug development and future clinical practice", PLoS ONE, 2009, vol. 4, pp. 1-9.

The methodologies are usually compared with the reference method, which is the Sanger sequencing of the whole virus, or of at least the NS5B region or 5'UTR-core/E1 region (Simmods et al. supra). Although the sequencing is considered the reference method, it implies the disadvantages of miss-readings due to the fact that the resulting sequence corresponds to an average of the sequences in an isolated sample. Thus, co-infections (infections with more than one HCV subtype at the same time) cannot be detected. In addition, a cloning and sequencing method to detect co-infections implies long analytical times and expensive costs, thus making it no practical in commercial kits.

Although all the existing kits based on semi-automatically sequencing, quantitative PCR, or reverse hybridization, have a high success rate in the HCV determination, there are also some limitation making them no infallible and leading to some erroneous determinations.

In effect, there are some subtypes difficulty distinguishable between each other, for examples subtypes 1a and 1 b, and there exist some false positives and false negatives. In addition, the above-mentioned kits do not allow the determination of multiple infections (co-infections) in case the subject is infected with an accompanying additional genotype or subtype in a low load or proportion.

But, there exists also an additional level of complexity in the infections with HCV that makes much more difficult the correct determination of the genotype or sub-genotype (subtype), in particular the possibility of an infection with a recombinant virus. The existence of recombinant variants of HCV is due to the fact that in patients co-infected with more than one genotypes or subtypes, recombination takes place between all these variants leading to an "hybrid" genotype or subtype, making difficult the determination of the real infecting variants. As above indicated, the determination of the real variant is of special importance in order to adapt or better prescribe a medical treatment.

It is, hence, of great interest to further develop improved genotypic assays for detecting the specific variants in HCV infected patients in order to better diagnose the subjects, and in order to detect resistance-associated mutations of the virus with higher sensitivity, with the aim of further predicting the responses to HCV prescribed treatments.

SUMMARY OF THE INVENTION

The present invention provides primers and methods using them for the genotyping and subtyping of Human Hepatitis C Virus (HCV) containing samples. The primers of the present invention provide robust clinical sensitivity and specificity, and provide also high throughput and efficient workflow.

In a first aspect the invention provides a set of primers for reverse transcribing (retrotranscribing) and amplifying the regions 5'-UTR and a fragment of core (5'-core) of the HCV RNA of an isolated sample, said combination including at least an oligonucleotide of formula (I)

$(N)_m$—Z     (I), as a reverse primer, wherein

Z is an oligonucleotide consisting in SEQ ID NO: 1 (5'-CTAGTCGCGCGCACACCCA-3'), m is an integer ranging from 0 to 25 nucleotides, and N is a nucleotide selected from A, T, C, G, and a forward primer capable of hybridizing to the 5'-UTR-Core portion of HCV, wherein the combination of primers is capable of generating a fragment comprising from nucleotides 146 to 490 of SEQ ID NO: 2.

The $(N)_m$-Z sequence or formula (I), being Z as defined above, can also be referred in the present application as SEQ ID NO: 15.

It has been found that the combination of primers of the first aspect of the invention is capable of generating a fragment identical to the one comprising from nucleotides 146 to 490 of SEQ ID NO: 2 when tested in front of a subtype 1a of HCV.

SEQ ID NO: 2 corresponds to the region comprising from nucleotide 1 to 914 of consensus sequence of the isolate H77 (GenBank accession number AF009606, version 1 of 18 Jun. 2009). This region encompasses the whole regions 5'-UTR and Core of the genome of the virus, and the numbering is established according to the system starting at 1 for the first nucleotide of the 5'-UTR. An in-depth standardized numbering system for HCV nucleotides, proteins and epitopes is exposed in the document of Kuiken et al., "A Comprehensive System for Consistent Numbering of HCV Sequences, Proteins and Epitopes", *Hepatology* —2006, DOI 10.1002/hep.21377, pp. 1355-1361. The sequence of the isolate H77 corresponds to a Hepatitis C virus subtype 1a polyprotein gene, complete cds, with 9646 bp RNA linear. Kuiken et al. (supra) also establishes the numbering system for other HCV variants already disclosed in the state of the art as well as for those to be identified in the future. In particular, it is disclosed that while the numbering system is based on a genotype 1a reference sequence, when several sequence locator tools are used with the different existing HCV genotypes, these tools align the sequences of all of them unambiguously to the reference sequence. From this reference, therefore, one can conclude that all HCV variants will include a 5'-UTR-Core region with some deletions, insertions, substitutions when compared with the same region in genotype 1a reference. If said sequence includes insertions or deletions, Kuiken et al. criteria also contemplate how to cite this modification in respect of the reference sequence (subtype 1a) without changing the basic enumeration.

The set of primers according to the invention used for generating the fragment of the HCV genome including the region defined as 5'-UTR-Core may also be employed for amplifying this region in any of the other genotypes and subtypes of the HCV other than the genotype 1a. Thus with only few selected primers a confidence amplification of any of the variants of a sample of a subject is got. Such amplification gives rise to a fragment of the viral genome region with a length comprising at least 344 nucleotide positions of the 5'-UTR-Core, and the nucleotides of the forward and reverse primers, wherein for nucleotide position is to be understood as including any nucleotide or a deletion or gap of a nucleotide in respect of the reference region of genotype 1a. That is, if a gap of one nucleotide is located (relative to the reference sequence) the preceding and the next nucleotides will not change the numeration received according to the reference sequence, and the generated fragment will be one nucleotide shorter, but that can be aligned with the global nucleotide positions of the reference sequence not carrying said deletion. In the same way, if one nucleotide is inserted with respect to the reference sequence, preceding and following nucleotides will not change the numeration and then the generated fragment will be longer and it will include, apart of the nucleotide positions of the reference sequence, the additional ones. For an example of the numbering of insertions and deletions relative to the reference sequence see Kuiken et al. (supra).

In other words, although in the present invention the generated fragment is defined referring to the SEQ ID NO: 2, that corresponds to an isolate classified as subtype 1a, if the HCV variant in the tested sample is from a different genotype or subtype among the genotypes, amplification will also occur and a fragment comprising at least the corresponding nucleotides from 146 to 490 of SEQ ID NO: 2 in the tested variants will be present. If said sequence includes insertions or deletions, in respect of the reference sequence (subtype 1a) this will be detected by alignment tools and enumeration of the sequence variant can be performed following Kuiken et al. criteria if needed.

Another aspect of the invention is an oligonucleotide of formula (I) as defined above.

Another aspect of the invention is a set of primers comprising the oligonucleotide of formula (I) as defined above. Another aspect of the invention is a composition comprising the oligonucleotide of formula (I).

A further aspect of the invention is a set of primers comprising at least an oligonucleotide of formula (II).

$(N)_m$—F     (II), as a reverse primer, wherein

F is an oligonucleotide consisting in SEQ ID NO: 5 (5'-TTNGADGAGCADGATGTWATBAGCTC-3'), in which N means Adenine (A), Cytosine (C), Guanine (G) or Thymine (T);

D means G, A or T;

W means A or T,

B means G, T or C, and m is an integer ranging from 0 to 25 nucleotides; and a forward primer capable of hybridizing to the NS5B portion of HCV, wherein the set of primers is capable of generating a fragment comprising from nucleotides 653 to 1106 of SEQ ID NO: 6.

It has been found that the combination of primers of this aspect of the invention is capable of generating a fragment identical to the one comprising from nucleotides 653 to 1106 of SEQ ID NO: 6 when tested in front of a subtype 1a.

SEQ ID NO: 6 corresponds to the region comprising from nucleotide 7602 to 9377 of consensus sequence of the isolate H77 disclosed above (GenBank accession number AF009606, version 1 of 18 Jun. 2009). This region encompasses the whole NS5B region of the genome of the virus, and the numbering is established according to the system starting at 1 for the first nucleotide of the 5'-UTR as above exposed. Therefore, in respect of the consensus sequence of the isolate H77, the set of primers is capable of generating a fragment comprising from nucleotides 8254 to 8707 of the consensus. This generated fragment, when indicated in respect of SEQ ID NO: 6 corresponds to a fragment comprising from nucleotides 653 to 1106 of said SEQ ID NO: 6 For the NS5B region the generated fragment is defined referring to the SEQ ID NO: 6, that corresponds to an isolate classified as subtype 1a. As indicated for SEQ ID NO: 2 and considering the established nomenclature from the Kuiken et al. (supra) reference, the other variants (genotypes or even subtypes among genotypes) of HCV may include in the NS5B region some deletions, insertions substitutions when compared with the same region in genotype 1a reference. If said sequence includes insertions or deletions, Kuiken et al. criteria also contemplate how to cite this modification in respect of the reference sequence (subtype 1a) without changing the basic enumeration.

The set of primers according to the invention used for generating the fragment of the HCV genome including the region defined as NS5B region, may also be employed for amplifying this region in any of the other genotypes and subtypes of the HCV other than the genotype 1a In other words, if the HCV variant in the tested sample is different than genotype 1a, amplification will also occur and a fragment comprising at least the corresponding in the tested variants nucleotides 653 to 1106 of SEQ ID NO: 6 will be present or, which is the same, the corresponding fragment from nucleotides 8254 to 8707 of the consensus sequence of the isolate H77. As before, the primers will amplify the corresponding sequence and if said sequence includes insertions or deletions, Kuiken et al. (supra) proposal contemplates how to cite this modification in respect of the reference sequence (genotype 1a) without changing the basic enumeration. Thus, the set of primers according to the invention used for generating the fragment of the HCV genome including the region defined as NS5B, give raise to a fragment of this genome region of the virus with a length that comprises at least 354 nucleotide positions of this region and the nucleotides of the forward and reverse primers, wherein for nucleotide position is to be understood as including any nucleotide or a deletion or gap of a nucleotide in respect of the reference region of genotype 1a.

Another aspect of the invention is an oligonucleotide of formula (II) as above disclosed. This formula (II) can also be defined as an oligonucleotide of SEQ ID NO: 16, including F as SEQ ID NO: 5, N as a nucleotide selected from A, T, C, G, and wherein m is from 0 to 25.

Another aspect of the invention is a set of primers comprising the oligonucleotide of formula (II) as defined above. Another aspect of the invention is a composition comprising the oligonucleotide of formula (II).

These sets of primers of the invention, used in combination, allow reverse transcribing (reverse transcription) and amplifying those key regions of the HCV RNA including the mutations existing between the genotypes and subtypes of the virus. In addition these primers are specific enough of these key informative regions, thus giving rise to amplicons of high purity that can then be sequenced with a high confidence level in order to determine the real HCV variant (genotype, subtype) or variants in a sample.

Another aspect of the invention is an oligonucleotide consisting in SEQ ID NO: 7 (5'-CNTAYGAYACCMGNTGYTTTGACTC-3'), wherein N means Adenine (A), Cytosine (C), Guanine (G) or Thymine (T); Y means T or C; and M means A or C.

Yet in another aspect the invention provides a set of primers comprising the oligonucleotide consisting in SEQ ID NO: 7 as forward primer, and a reverse primer capable of hybridizing to the NS5B portion of HCV, wherein the set of primers is capable of generating a fragment comprising from nucleotides 653 to 1040 of SEQ ID NO: 6.

This fragment from nucleotides 653 to 1040 of SEQ ID NO: 6 is the equivalent (or corresponding) fragment, indicated in respect of the consensus sequence of the isolate H77, comprising from nucleotides 8254 to 8641 of the consensus. As above exposed the nucleotide numbering is established according to the system starting at 1 for the first nucleotide of the 5'-UTR of consensus sequence H77 (GenBank accession number AF009606).

Yet another aspect of the invention is an oligonucleotide consisting in SEQ ID NO: 8 (5'-GARTAYCTGGTCATAGCNTCCGTGAA-3'), wherein R means Adenine (A) or Guanine (G); Y means Thymine (T) or Cytosine (C); and N means Adenine (A), Cytosine (C), Guanine (G) or Thymine (T).

These set of primers including the oligonucleotide consisting in SEQ ID NO: 7 as forward primer, and spanning several codons of the NS5B portion of HCV for generating a fragment comprising from nucleotides 653 to 1040 of SEQ ID NO: 6, are especially useful to enhance the purity of any previously reverse transcribed and amplified fragment of this same region. The resulting amplicon still contains the key regions including the mutations between genotypes and subtypes of the HCV. Therefore, they provide a highly pure sample with the aim of further sequencing it and determining the HCV variant.

As will be illustrated in the Examples below all these sets of primers, used in combination in an in vitro method for determining the genotype or subtype of HCV in a sample, allow better scores in the percentage of correct identifications in relation with the other kits and methods of the prior art. These results are even better than those achieved with the reference sequencing methods in the special cases of co-infected analyzed samples.

Thus, another aspect of the invention is a kit for detecting one or more HCV sequence variants comprising at least one of the sets of primers as defined above.

In another aspect the invention provides the use of any of the above-mentioned set of primers alone or in combination for detecting one or more HCV sequence variants.

A further aspect of the invention provides an in vitro method for determining in an isolated sample of a subject the presence of one or more Human Hepatitis C Virus (HCV) sequence variants comprising:

i) reverse transcribing and amplifying HCV RNAs molecules by RT-PCR using the following set of primers:

a) a set of primers as defined above and comprising an oligonucleotide of formula (I) as reverse primer, and a forward primer capable of hybridizing to the 5'-UTR-Core portion of HCV, wherein the combination of primers is capable of generating a fragment comprising from nucleotides 146 to 490 of SEQ ID NO: 2, and b) a set of primers comprising an oligonucleotide of formula (II) as reverse primer, and a forward primer capable of hybridizing to the NS5B portion of HCV, wherein the set of primers is capable of generating a fragment comprising from nucleotides 653 to 1106 of SEQ ID NO: 6, ii) further amplifying the fragments generated in step i) by a second polymerase chain reaction (PCR) using the following set of primers:

c) a set of primers as defined above comprising an oligonucleotide of formula (I) as reverse primer and a forward primer capable of hybridizing to the 5'-UTR-Core portion of HCV, wherein the combination of primers is capable of generating a fragment comprising from nucleotides 146 to 490 of SEQ ID NO: 2, and d) a set of primers comprising the oligonucleotide consisting in SEQ ID NO: 7 as forward primer, and a reverse primer capable of hybridizing to the NS5B portion of HCV, wherein the set of primers is capable of generating a fragment comprising from nucleotides 653 to 1040 of SEQ ID NO: 6, and iii) sequencing the amplified fragments obtained in step ii).

In this specific case, in which some of the primers are used in both steps i) and ii), the PCR performed in step ii) is commonly known as hemi-nested-PCR.

DETAILED DESCRIPTION OF THE INVENTION

Figure 1:
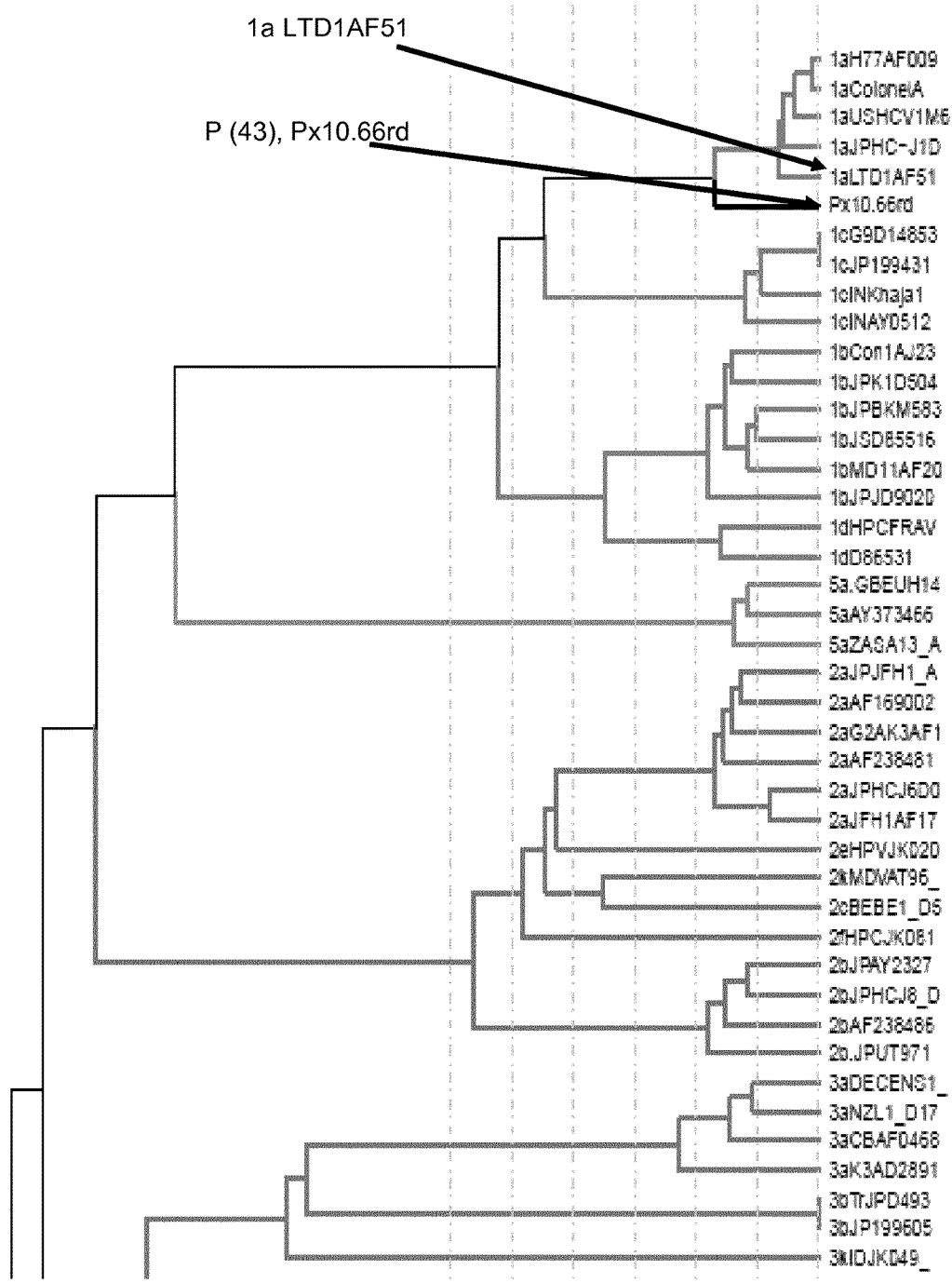
FIG. 1 is a phylogenetic tree diagram of the different subtypes of HCV showing the emplacement of one of the amplified sequences detected in a test sample of a patient (patient P43, Px10.66rd) infected with 1a subtype.
Figure 1:
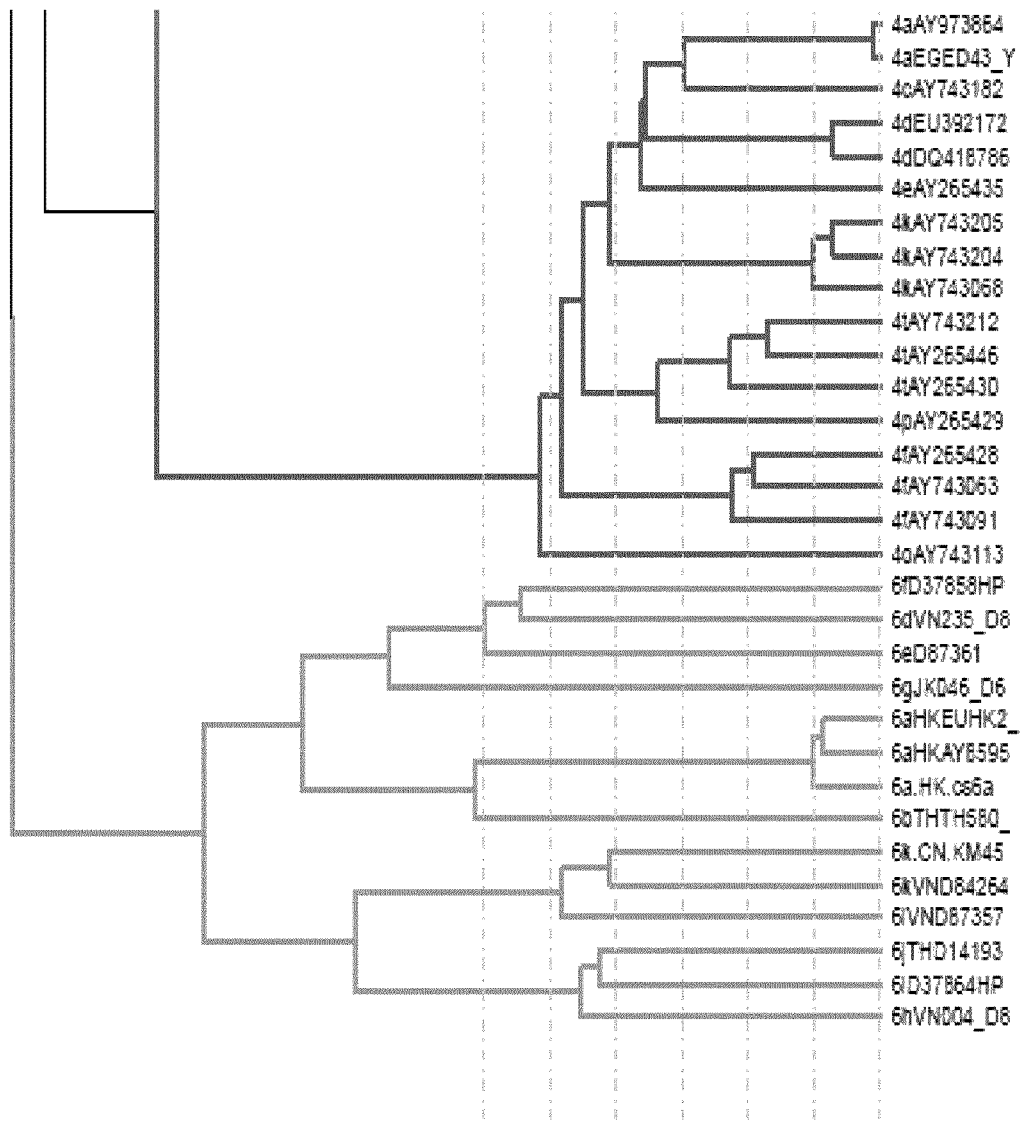

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art.

"HCV variant sequence" relates to the clade or genotype (including subtypes into the genotype) of the specific HCV, which is classified according to a known pattern listing all the identified variants of the virus. A "genotype" is defined as the genetic makeup of a cell, an organism (including viruses), or an individual (i.e. the specific allele makeup of the individual) usually with reference to a specific character under consideration. In the majority of the cases a variant sequence and an identified genotype are interchangeable terms. On the other side, a variant sequence can be the result of genetic recombination of two identified HCV genotypes. In this later case, the HCV variant sequence is not equivalent to genotype or clade, but to mixtures of genotypes. HCV genotypes differ from each other by 31% to 33% at nucleotide level. A "subtype" or "subgenotype" (used interchangeable herein) is defined as a sequence variant at nucleotide levels into a specific genotype. HCV subtypes differ from each other by 20% to 25% at nucleotide level, although pertaining to the same genotype.

As used herein the term "genotyping" or "determination of a virus variant sequence" is the process of determining differences in the genetic make-up (or genotype) of an individual virus by examining the DNA or RNA sequence of the virus using biological assays and comparing it to another virus sequence or a reference sequence. Traditionally, genotyping is the use of DNA or RNA sequences to define biological populations by use of molecular tools. It does not usually involve defining the genes of an individual.

As used herein, the term "amplicon" refers to a product of an amplification reaction. An example of an amplicon is a DNA or an RNA product (usually a segment of a gene, DNA or RNA) produced as a result of PCR, real-time PCR, reverse transcription PCR (RT-PCR), competitive Real Time-PCR, ligase chain reaction (LCR), gap LCR, strand displacement amplification (SDA), nucleic acid sequence based amplification (NASBA), transcription-mediated amplification (TMA), or the like. As used herein, the phrases "amplification," "amplification method," or "amplification reaction," are used interchangeably and refer to a method or process that increases the representation of a population of specific nucleic acid (all types of DNA or RNA) sequences (such as a target sequence or a target nucleic acid) in a test sample. Examples of amplification methods that can be used in the present invention include, but are not limited to, PCR, real-time PCR, reverse transcription PCR (RT-PCR), competitive Real Time-PCR, ligase chain reaction (LCR), gap LCR, strand displacement amplification (SDA), nucleic acid sequence based amplification (NASBA), transcription-mediated amplification (TMA), and the like, all of which are known to one skilled in the art.

As used herein, the term "hybridization" refers to the formation of complexes between nucleic acid sequences which are sufficiently complementary to form complexes via Watson-Crick base pairing or non-canonical base pairing. For example, when a primer "hybridizes" with a target sequence (template), such complexes (or hybrids) are sufficiently stable to serve the priming function required by, e.g., the DNA polymerase, to initiate DNA synthesis. It will be appreciated by one skilled in the art that hybridizing sequences need not to have perfect complementarities to provide stable hybrids. In many situations, stable hybrids will be formed when fewer than about 10% of the bases are mismatched. Accordingly, as used herein, the term "complementary" refers to an oligonucleotide that forms a stable duplex with its complement under assay conditions, generally where there is about 80%, about 81%, about 82%, about 83%, about 84%, about 85%, about 86%, about 87%, about 88%, about 89%, about 90%, about 91%, about 92%, about 93%, about 94% about 95%, about 96%, about 97%, about 98%, or about 99% Watson-Crick base pairments. Those skilled in the art understand how to estimate and adjust the stringency of hybridization conditions such that sequences having at least a desired level of complementarities will stably hybridize, while those having lower complementarities will not.

The term "primer" refers to an oligonucleotide capable of acting as a point of initiation of synthesis of a primer extension product that is a complementary strand of nucleic acid (all types of DNA or RNA), when placed under suitable amplification conditions (e.g., buffer, salt, temperature and pH) in the presence of nucleotides and an agent for nucleic acid polymerization (e.g., a DNA-dependent or RNA-dependent polymerase). The primer can be single-stranded or double-stranded. If double-stranded, the primer may first be treated (e.g., denatured) to allow separation of its strands before being used to prepare extension products. Such a denaturizing step is typically performed using heat, but may alternatively be carried out using alkali, followed by neutralization. The primers of the present invention may have a length of about 15 to about 50 nucleotides in length, preferably from about 20 to about 40 nucleotides in length, most preferably, from about 22 to about 30 nucleotides in length. The primers of the present invention can contain additional nucleotides in addition to those described in more detail herein. The phrase "forward primer" refers to a primer that hybridizes (or anneals) with the target sequence (e.g., template strand). The phrase "reverse primer" refers to a primer that hybridizes (or anneals) to the complementary strand of the target sequence. The forward primer hybridizes with the target sequence 5' with respect to the reverse primer.

As used herein, the expression "primer set" (set of primers) refers to two or more primers which together are capable of priming the amplification of a target sequence or target nucleic acid of interest (e.g., a target sequence within the HCV). In certain embodiments, the term "primer set" refers to a pair of primers including a 5' (upstream) primer (or forward primer) that hybridizes with the complementary 5'-end of the target sequence or target nucleic acid to be amplified and a 3' (downstream) primer (or reverse primer) that hybridizes with the complement of the target sequence or target nucleic acid to be amplified. Such primer sets or primer pairs are particularly useful in PCR amplification reactions.

An "oligonucleotide" is to be understood as a short, single-stranded DNA or RNA molecule (usually from 2 to 20 nucleotides) that have a wide range of applications in genetic testing, research, and forensics. In fact, a primer is an oligonucleotide. Commonly made in the laboratory by solid-phase chemical synthesis, these small bits of nucleic acids can be manufactured with any user-specified sequence, and so are vital for artificial gene synthesis, polymerase chain reaction (PCR), DNA sequencing, library construction and as molecular probes. In nature, oligonucleotides are usually found as small RNA molecules that function in the regulation of gene expression (e.g. microRNA), or are degradation intermediates derived from the breakdown of larger nucleic acid molecules. Oligonucleotides readily bind, in a sequence-specific manner, to their respective complementary oligonucleotides, DNA, or RNA to form duplexes or, less often, hybrids of a higher order.

If not expressed to the contrary, when in the present invention a sequence of a primer or of a fragment of the HCV is indicated, the 5'-end of the sequence corresponds to the first nucleotide indicated in the sequence, according to the accepted standard nomenclature in which the nucleotide sequences are expressed in the 5' to 3' sense (following Kuiken et al. criteria as deeply discussed above).

Sometimes degenerate primers are used. These are actually mixtures of similar, but not identical primers. They may be convenient if the genetic region at which the primer hybridizes shows variation in particular nucleotide positions when comparing different isolates (genotypes or subtypes).

The phrases "target sequence" and "target nucleic acid" are used interchangeably herein and refer to the sequence whose presence or absence is desired to be detected. In the context of the present invention, a target sequence preferably includes a nucleic acid sequence to which one or more primers will complex. The target sequence can also include a probe-hybridizing region with which a probe will form a stable hybrid under appropriate amplification conditions. As will be recognized by one of ordinary skill in the art, a target sequence may be single-stranded or double-stranded.

As used herein, the term "test sample" generally refers to a biological material being tested for and/or suspected of containing an analyte of interest, such as an HCV nucleotide sequence. The test sample may be derived from any biological source, such as, a cervical, vaginal or anal swab or brush, or a physiological fluid including, but not limited to, whole blood, serum, plasma, interstitial fluid, saliva, ocular lens fluid, cerebral spinal fluid, sweat, urine, milk, ascites fluid, mucus, nasal fluid, sputum, synovial fluid, peritoneal fluid, vaginal fluid, menses, amniotic fluid, semen, and so forth. The test sample may be used directly as obtained from the biological source or following a pretreatment to modify the character of the sample. For example, such pretreatment may include preparing plasma from blood, diluting viscous fluids, and so forth. Methods of pretreatment may also involve filtration, precipitation, dilution, distillation, mixing, concentration, lyophilization, inactivation of interfering components, the addition of reagents, lysing, etc. Moreover, it may also be beneficial to modify a solid test sample to form a liquid medium or to release the analyte. Preferably, the sample may be serum or plasma.

The main problem when designing primers for HCV reverse transcription and amplification for further sequencing is the high number of genotypes and subtypes identified for HCV. This renders the selection of the genomic region of interest a cumbersome task.

In principle, primers must be designed on regions highly conserved across viruses. This is essential to ensure reliable performance of the designed primers to amplify the genomic region of interest without substantial risk of failure. Failure of the amplification is mainly due to mutation at the target region that renders the primer unable to bind. This task is even more difficult when designing primers for HCV genotyping, since the primers must be designed so that the same primer set can be used for sequencing the target region for multiple clades.

Surprisingly, the oligonucleotides of the present invention have been designed so that they can be used as primers able for reverse transcribing and amplifying those key regions of the HCV RNA sequence, including the mutations existing between the genotypes and subtypes of the virus. In addition these primers are specific enough for these key regions, thus giving raise to amplicons of high purity that can then be sequenced with a high confidence level in order to determine the real HCV variant (genotype, subtype) or variants in a sample.

In an embodiment of the oligonucleotide of formula (I), m is 20. In another embodiment m is 10, and yet in another embodiment m is 5. In other embodiments m is selected from 1, 2, 3, 4, 6, 7, 8, 9, 11, 12, 13, 14, 15, 16, 17, 18, 19, 21, 22, 23, 24 and 25.

In a preferred embodiment the oligonucleotide of formula (I) consists in SEQ ID NO: 1, thus it is an oligonucleotide of formula (I) in which m is 0.

When the oligonucleotide of formula (I) is a reverse primer that forms part of a set of primers according to the invention, the forward primer capable of hybridizing to the 5'-UTR-Core portion of HCV consists in a sequence selected from SEQ ID NO: 3 and SEQ ID NO: 4.

In an embodiment of the oligonucleotide of formula (II), m is 20. In another embodiment m is 10, and yet in another embodiment m is 5. In other embodiments m is selected from 1, 2, 3, 4, 6, 7, 8, 9, 11, 12, 13, 14, 15, 16, 17, 18, 19, 21, 22, 23, 24 and 25.

Another embodiment is an oligonucleotide of formula (II) in which F is an oligonucleotide consisting in SEQ ID NO: 5 (5'-TTNGADGAGCADGATGTWATBAGCTC-3'), that is, m is 0.

Indeed, SEQ ID NO: 5 includes 216 different sequences considering the multiple combinations of the values N, D, W, and B. Preferred sequences are selected from the group consisting of SEQ ID NO: 36 to SEQ ID NO: 53. That is, TTAGATGAGCATGATGTAATGAGCTC (SEQ ID NO: 36), TTAGATGAGCATGATGTAATTAGCTC (SEQ ID NO: 37), TTAGATGAGCATGATGTAATCAGCTC (SEQ ID NO: 38), TTAGATGAGCATGATGTTATGAGCTC (SEQ ID NO: 39), TTAGATGAGCATGATGTTATTAGCTC (SEQ ID NO: 40), TTAGATGAGCATGATGTTATCAGCTC (SEQ ID NO: 41), TTAGATGAGCAGGATGTAATGAGCTC (SEQ ID NO: 42), TTAGATGAGCAGGATGTAATTAGCTC (SEQ ID NO: 43), TTAGATGAGCAGGATGTAATCAGCTC (SEQ ID NO: 44), TTAGATGAGCAGGATGTTATGAGCTC (SEQ ID NO: 45), TTAGATGAGCAGGATGTTATTAGCTC (SEQ ID NO: 46), TTAGATGAGCAGGATGTTATCAGCTC (SEQ ID NO: 47), TTAGATGAGCAAGATGTAATGAGCTC (SEQ ID NO: 48), TTAGATGAGCAAGATGTAATTAGCTC (SEQ ID NO: 49), TTAGATGAGCAAGATGTAATCAGCTC (SEQ ID NO: 50), TTAGATGAGCAAGATGTTATGAGCTC (SEQ ID NO: 51), TTAGATGAGCAAGATGTTATTAGCTC (SEQ ID NO: 52), and TTAGATGAGCAAGATGTTATCAGCTC (SEQ ID NO: 53)

In a preferred embodiment, when the oligonucleotide of formula (II) is a reverse primer that forms part of a set of primers, the forward primer capable of hybridizing to the NS5B portion of HCV consists in SEQ ID NO: 7 (5'-CNTAYGAYACCMGNTGYTTTGACTC-3'), wherein N means Adenine (A), Cytosine (C), Guanine (G) or Thymine (T); Y means T or C; and M means A or C.

SEQ ID NO: 7 includes 256 different sequences considering the multiple combinations of the values N, Y, and M. Preferred sequences are selected from the group consisting of SEQ ID NO: 54 to SEQ ID NO: 69. That is, CATATGATACCAGATGCTTTGACTC (SEQ ID NO: 54), CATATGATACCAGATGTTTTGACTC (SEQ ID NO: 55), CATATGATACCAGTTGCTTTGACTC (SEQ ID NO: 56), CATATGATACCAGTTGTTTTGACTC (SEQ ID NO: 57), CATATGATACCAGGTGCTTTGACTC (SEQ ID NO: 58), CATATGATACCAGGTGTTTTGACTC (SEQ ID NO: 59), CATATGATACCAGCTGCTTTGACTC (SEQ ID NO: 60), CATATGATACCAGCTGTTTTGACTC (SEQ ID NO: 61), CATATGATACCCGATGCTTTGACTC (SEQ ID NO: 62), CATATGATACCCGATGTTTTGACTC (SEQ ID NO: 63), CATATGATACCCGTTGCTTTGACTC (SEQ ID NO: 64), CATATGATACCCGTTGTTTTGACTC (SEQ ID NO:65), CATATGATACCCGGTGCTTTGACTC (SEQ ID NO: 66), CATATGATACCCGGTGTTTTGACTC (SEQ ID NO: 67), CATATGATACCCGCTGCTTTGACTC (SEQ ID NO: 68), CATATGATACCCGCTGTTTTGACTC (SEQ ID NO: 69)

When an oligonucleotide of formula (II) is a reverse primer, preferred sequences are those selected from the group consisting of SEQ ID NO: 36 to SEQ ID NO: 53, and mixtures thereof. In a set of primers including degenerate oligonucleotides, mixtures of all the primers are employed in order to assure the amplification of all variants of HCV in a sample.

In the same way, when as forward primer a degenerate oligonucleotide consisting in SEQ ID NO: 7 is used, preferred sequences are selected from the group consisting of SEQ ID NO: 54 to SEQ ID NO: 69, and mixtures thereof.

The invention also provides a set of primers specially designed for performing hemi-nested amplifications of previously reverse transcribed and amplified regions (fragments). This set of primers includes a primer or oligonucleotide consisting in SEQ ID NO: 7 as forward primer, and a reverse primer capable of hybridizing to the NS5B portion of HCV, the set generating a fragment comprising from nucleotide 653 to 1040 of SEQ ID NO: 6.

In a preferred embodiment, said reverse primer in the set consists in an oligonucleotide of SEQ ID NO: 8 (Bo8641).

Indeed, the oligonucleotide of SEQ ID NO: 8 represents a group of 16 sequences, when considering the multiple combinations of the values R, Y and N. Preferred sequences are selected from the group consisting of SEQ ID NO: 70 to SEQ ID NO: 73. That is, GAATATCTGGTCATAGCATCCGTGAA (SEQ ID NO: 70), GAATATCTGGTCATAGCTTCCGTGAA (SEQ ID NO: 71), GAATATCTGGTCATAGCGTCCGTGAA (SEQ ID NO: 72), and GAATATCTGGTCATAGCCTCCGTGAA (SEQ ID NO: 73).

As above exposed, when as forward primer a degenerate oligonucleotide consisting in SEQ ID NO: 7 is used, preferred sequences are selected from the group consisting of SEQ ID NO: 54 to SEQ ID NO: 69, and mixtures thereof.

In the same way, when as reverse primer a degenerate oligonucleotide consisting in SEQ ID NO: 8 is used, preferred sequences are selected from the group consisting of SEQ ID NO: 70 to SEQ ID NO: 73, and mixtures thereof.

With only these three types of sets of primers, employed in combination in a method for determining the presence of one or more HCV sequence variants in a sample, it is possible to detect any of the HCV genotypes or subtypes, even though a specific variant is present at very low levels in said sample.

All these sets of primers may form part of a kit for genotyping HCV, in any of the possible combinations of the sets, or they can be conceived as independent reagents useful in a method for genotyping HCV. That is, a kit may contain only one of the set of primers, or two, or three.

The kit may additionally comprise the means (additives, solvents) to perform the reverse transcription and/or amplification of a desired gene fragment, including the buffer solution, the enzymes (polymerases), nucleotide mixtures (dNTPs, ddNTPs), additives to improve visualization of an amplified fragment in an electrophoresis gel, such as probes (specific or not). Some of the components suitable to form part of the kits of the invention are provided in the examples. In addition the sets of primers according to the invention may also be integrants or reagents of different commercial kits. Examples of commercial kits include the Transcriptor one-step RT-PCR Kit of Roche, or the FastStart High Fidelity PCR System, dNTPack (Roche).

The present invention also provides an in vitro method for determining the sequence variant of HCV in an isolated sample of a subject, in which method the sets of primers disclosed above are used in combination for genotyping those critical regions including the meaningful mutations allowing distinction between genotypes and subtypes into a genotype.

In a preferred embodiment of this method, step i) of reverse transcribing and amplifying HCV RNAs molecules is performed using the following set of primers:

a) a reverse primer of formula (I) and a forward primer which consists in SEQ ID NO: 3 (UTR45), and
b) a reverse primer of formula (II) and a forward primer which consists in SEQ ID NO: 7 (Bo8245).

In a most preferred embodiment the reverse primer in a) consists in SEQ ID NO: 1, and the reverse primer in b) consists in SEQ ID NO: 5. Preferred reverse primers are selected from the group consisting of SEQ ID NO: 36 to SEQ ID NO: 53 and mixtures thereof.

In another embodiment of the method according to the invention, step ii) is performed using the following sets of primers:
a) a reverse primer of formula (I) and forward primer which consists in SEQ ID NO: 4, and
b) a forward primer consisting in SEQ ID NO: 7 and a reverse primer consisting in SEQ ID NO: 8.

In this method, preferred forward primers generically defined as SEQ ID NO: 7 are selected from the group consisting of SEQD ID NO: 54 to SEQ ID NO: 69, and mixtures thereof. Also preferred reverse primers generically defined as SEQ ID NO: 8 are selected from the group consisting of SEQ ID NO: 70 to SEQ ID NO: 73, and mixtures thereof.

Once the fragments of interest have been amplified, they are further submitted to a sequencing step. This step may be carried out by any of the known sequencing technologies, such as the Sanger method or the pyrosequencing method.

If the Sanger method is elected, the pair of primers defined by the reverse primer of formula (I), preferably consisting in SEQ ID NO: 1, with a forward primer of SEQ ID NO: 4, may be used for the sequencing of the 5'-UTR-core zone (region) of the HCV variants. In parallel, the pair of primers defined by the forward primer consisting in SEQ ID NO:7 with the reverse primer consisting in SEQ ID NO: 8 may be employed for sequencing the NS5B zone (region) of the HCV variants.

If pyrosequencing is employed, it is highly preferred any high-throughput long read sequencing technology known in the art that allows sequencing many target nucleic acid molecules in parallel by generating thousands of clonal reads. In a preferred embodiment of the present invention, the sequencing technology used is the so-called 454 sequencing, described in detail in the examples below.

454 sequencing is a massively parallel sequencing technology to generate thousands of clonal reads from one or multiple subjects in a single sequencing run. Therefore, simultaneous assessment of multiple HCV variants with high sensitivity can be achieved.

Surprisingly, the primers of the present invention, allow the sequencing of the whole critical zones of HCV using as few as four sets of primers, generally defined in a group of three types of sets.

In a preferred embodiment, when performing the method of the invention by 454 sequencing, the primers of the invention used in the hemi-nested PCR (step ii) comprise at their 5' section a universal oligonucleotide sequence corresponding to a fragment of the M13 bacteriophage. The fragment sequence of the M13 bacteriophage is different for the forward and the reverse primers of the hemi-nested amplification, being, GTTGTAAAACGACGGCCAGT (SEQ ID NO: 9) for forward primers, and CACAGGAAACAGCTATGACC (SEQ ID NO: 10) for reverse primers.

If the last step (iii) of sequencing is to be performed using the 454 high-throughput sequencing technology, the method may optionally include the performance of a new PCR reaction with the universal primers (of Roche property) with the sequences CGTATCGCCTCCCTCGCGCCAGTTGTAAAACGACGGCCAGT (SEQ ID NO: 11) as forward primer, and CTATGCGCCTTGCCAGCCCGCCACAGGAAACAGCTATGACC (SEQ ID NO: 12) as reverse primer. These universal primers allow amplifying the fragments to be further sequenced in order the amplicons finally include in the 5' section the adapters (oligos) CGTATCGCCTCCCTCGCGCCA (SEQ ID NO: 13) and CTATGCGCCTTGCCAGCCCGC (SEQ ID NO: 14) needed for pyrosequencing or any other type of universal sequencing. Indeed, the adapters at the 5' section correspond to sequences that are complementary to an oligonucleotide immobilized on a bead. In said case, the adapters at the 5' section allow the amplicons to attach to beads to be further sequenced.

454 high-throughput sequencing technology could also be performed with the primers of the invention used in the hemi-nested amplification step ii), provided that the primers include also at its 5' section the adapters CGTATCGCCTCCCTCGCGCCA (SEQ ID NO: 13) for forward primers and CTATGCGCCTTGCCAGCCCGC (SEQ ID NO: 14) for reverse primers.

Utility of the 454 technology in the sequencing of HCV appears deeply disclosed in the document of Lauck M., et. al. "Analysis of hepatitis C virus intra-host diversity across the coding region by ultra-deep sequencing". *J. Virol.*— 2012, Epub (online publication, ahead of print). This reference states the utility of the Roche technology in the sequencing of HCV genome fragments, and shows the deep in which the technology can detect rare mutations of a specified subtype, namely the 1a of HCV. The primers used for performing reverse transcription and amplification are the ones of the SuperScript III High Fidelity One-Step RT-PCR kit (Invitrogen, Life Technologies, Carlsbad, Calif.). Then the amplicons are submitted to different methods for preparing them for the 454-sequencing.

Using any of the high-throughput long read sequencing technologies known in the art, the method of the invention may be used for the genotyping of the HCV sequence variants derived from at least a sample taken from a single patient in a very fast mode, as well as the HCV sequence variants derived from at least a sample taken from several patients without delay time of analysis and diagnosis.

In any of the embodiments of the method of the invention, a further step iv) of correlating the detected sequence variants with a pattern that associates the detected variant with HCV drug resistance may be added.

This additional step represents an interesting tool for clinicians which can rapidly prescribe the correct therapy or medical regimen for a given patient.

The method and primers of the invention imply the great advantage that co-infections with a low load of one of the HCV variants in a single sample may be detected, so that the most appropriate therapy for the patient is determined. The method and primers also allow the detection in a sample of recombinant HCV infections, thus also leading to the best therapy choice.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

Next examples allow putting on manifest the usability and advantages of the in vitro method according to the invention, in which method specific oligonucleotides of the invention acting as primers are employed.

Example 1. Comparative Results of Four Methodologies for HCV Genotyping

In this assay it was compared for 43 serum samples, the efficiency, reliability and sensitivity of the 3 competing methodologies for HCV subtyping, named Commercial technique a (CTa; Versant HCV Genotype 2.0, LiPA, Siemens, based on a line probe assay (LiPA) targeting both 5' UTR and core regions of HCV), Commercial Technique b (CTb; Real Time HCV Genotype II, Abbott, based on a real-time PCR targeting NS5B for subtyping 1a and 1 b and 5'UTR for the other genotypes) and the method according to the invention using the technology known as GS-Junior (or GS-Junior 454 deep-sequencing platform). The Sanger sequencing method was taken as a reference one accepting its inability to detect multiple infections when the minority subtype is below 20%. Sanger sequencing is a method of DNA sequencing based on the selective incorporation of chain-terminating dideoxynucleotides by DNA polymerase. A sequencing kit Bigdye terminator v1.1 cycle (Applied Biosystems, and a capillary automated DNA-sequencing instrument (Applied Biosystems) were used.

The comparative data for the 43 samples are summarized in Table 4.

Sample Extraction:

Blood from the 43 individuals infected with HCV and detectable HCV RNA levels above 100000 copies/mL was collected in Vacutainer tubes without additives. After coagulation, serum was obtained by low-speed centrifugation.

Viral RNA Extraction:

0.75 ml of serum of each of the tested individuals was used for automatic RNA extraction using Total Nucleic Acid Isolation kit (TNAI, Roche Diagnostics) according to the manufacturer's instructions.

1. A) Generation of amplicon libraries for the sequencing reaction with the GS-Junior technology (from Roche) to carry out the in vitro method of the invention:

For each of the 43 samples an amplicon was obtained of the 5'-UTR-Core region and an amplicon for the NS5B region.

Those primers not commercially available and in particular the primers (oligonucleotides) of the invention were obtained by standard chemical synthesis using any commercial kit for this purpose.

Performance of RT-PCR was as follows:

To a final volume of 50 μl the following ingredients were added: 10 μl of Buffer (5×) (Transcriptor one-step RT-PCR Kit, Roche), 1 μl (20 μM) of each of the primers (forward and reverse) for amplifying the 5'-UTR-Core or 1.5 μl (20 μM) of each of the degenerate primers (forward and reverse) for amplifying the NS5B region, 1 μl of polymerase (Transcriptor one-step RT-PCR kit, Roche) 5 μl of the sample containing viral RNA (test or control), the corresponding μl of RNase Free Water (Transcriptor one-step RT-PCR Kit, Roche) to a final volume of 50 μl. The mixtures were introduced in the thermocycler (Applied Biosystems).

RT-PCR cycles were:

For RT 30 minutes (min) at 50° C., and 7 min at 94° C.

For the PCR, coupled to the RT phase, 10 cycles of 10 seconds (sec) at 94° C., 30 sec at 50° C. and 1 min at 68° C., followed by 20 cycles of 10 sec at 94° C., 30 sec at 50° C., 1 min at 68° C. (increasing 5 seconds per cicle), followed by 7 min more at 68° C. to finally lower the temperature at 4° C.

Sequences of specific used primers are indicated in Table 1.

TABLE 1

Primers used in the RT-PCR (step i)

| HCV region | Forward primer | Reverse primer |
|---|---|---|
| 5'-UTR-Core | CTGTGAGGAACTAC TGTCTTCACGCAG (SEQ ID NO: 3) | CTAGTCGCGCGCAC ACCCA (SEQ ID NO: 1) |
| NS5B region | Primers of generic CNTAYGAYACCMGN TGYTTTGACTC (SEQ ID NO: 7). Mixture of oligonucleotides consisting in SEQ ID NO: 54 to SEQ ID NO: 69 | Primers of generic TTNGADGAGCADGA TGTWATBAGCTC (SEQ ID NO: 5). Mixture of oligonucleotides consisting in SEQ ID NO: 36 to SEQ ID NO: 53 |

Performance of the hemi-nested PCR (further amplification of fragments of the RT-PCR in order to get an amount to be sequenced) (step ii):

Each of the samples previously submitted to RT-PCR were further amplified in an hemi-nested PCR with the FastStart High Fidelity PCR System, dNTPack (Roche).

To a final volume of 50 μl the following ingredients were added: 5 μl of Buffer (10×, FastStart High Fidelity of Roche), 1 μl (20 μM) of each of the primers (forward and reverse) for amplifying the 5'-UTR-Core or 1.5 μl (20 μM) of each of the degenerate primers (forward and reverse) for amplifying the NS5B region, 0.5 μl of polymerase (FastStart High Fidelity PCR system, Roche) 1 μl (40 μM) dNTP, 2 μl of amplified DNA (5-250 ng), and the corresponding μl of RNase Free Water to a final volume of 50 μl. The mixtures were introduced in the thermocycler Applied Biosystems).

The amplification was carried out in the following way:

1 min at 95° C., followed by 30 cycles of 20 sec at 95° C. 20 sec at 55° C., 1 min at 72° C., and then after the last cycle 5 min at 72° C., to finally lower the temperature at 4° C.

Following Table 2 shows the primers used in the hemi-nested PCR. All of them included at their 5' section (end) an universal oligonucleotide sequence corresponding to a fragment of the M13 bacteriophage: GTTGTAAAACGACGGCCAGT (SEQ ID NO: 9) for the forward primers, and CACAGGAAACAGCTATGACC (SEQ ID NO: 10) for the reverse primers.

| HCV region | Forward primer | Reverse primer |
|---|---|---|
| 5'-UTR-Core | GTTGTAAAACGACG GCCAGTGTCTGCGG AACCGGTGAGTACA (SEQ ID NO: 17) | CACAGGAAACAGCT ATGACCCTAGTCGC GCGCACACCCA (SEQ ID NO: 18) |

-continued

| HCV region | Forward primer | Reverse primer |
|---|---|---|
| NS5B region | Oligonucleotides of generic sequence GTTGTAAAACGA CGGCCAGTCNTA YGAYACCMGNTG YTTTGACTC (SEQ ID NO: 19). Mixture of oligonucleotides consisting in SEQ ID NO: 9 immediately joined at the 5'-end of each of the sequences SEQ ID NO: 54 to SEQ ID NO: 69 | Oligonucleotides of generic sequence CACAGGAAACAG CTATGACCGART AYCTGGTCATAG CNTCCGTGAA (SEQ ID NO: 20) Mixture of oligonucleotides consisting in SEQ ID NO: 10 immediately joined at the 5'-end of each of the sequences SEQ ID NO: 70 to 73. |

Finally, in order to unequivocally and easily identify the samples to be sequenced using the 454 high-throughput sequencing technology, the hemi-nested amplified samples were submitted to a further PCR reaction with 55 base pairs (bp) primers exemplified in Table 3 and using the reagents of the FastStart High Fidelity PCR System, dNTPack (Roche):

TABLE 3

| Identification | Universal primers with adaptor oligos A or B + key + MID + M13 bacteriophage oligonucleotide sequence for forward (Fw) or reverse (RV) primers) |
|---|---|
| AFw1M13u (SEQ ID NO: 21) | CGTATCGCCTCCCTCGCGCCATCAGACGAGT GCGTGTTGTAAAACGACGGCCAGT |
| BRv1M13d (SEQ ID NO: 22) | CTATGCGCCTTGCCAGCCCGCTCAGACGAGT GCGTCACAGGAAACAGCTATGACC |
| AFw2M13u (SEQ ID NO: 23) | CGTATCGCCTCCCTCGCGCCATCAGACGCTC GACAGTTGTAAAACGACGGCCAGT |
| BRv2M13d (SEQ ID NO: 24) | CTATGCGCCTTGCCAGCCCGCTCAGACGCTC GACACACAGGAAACAGCTATGACC |
| AFw3M13u (SEQ ID NO: 25) | CGTATCGCCTCCCTCGCGCCATCAGAGACGC ACTCGTTGTAAAACGACGGCCAGT |
| BRv3M13d (SEQ ID NO: 26) | CTATGCGCCTTGCCAGCCCGCTCAGAGACGC ACTCCACAGGAAACAGCTATGACC |
| AFw4M13u (SEQ ID NO: 27) | CGTATCGCCTCCCTCGCGCCATCAGAGCACT GTAGGTTGTAAAACGACGGCCAGT |
| BRv4M13d (SEQ ID NO: 28) | CTATGCGCCTTGCCAGCCCGCTCAGAGCACT GTAGCACAGGAAACAGCTATGACC |
| AFw5M13u (SEQ ID NO: 29) | CGTATCGCCTCCCTCGCGCCATCAGATCAGA CACGGTTGTAAAACGACGGCCAGT |
| BRv5M13d (SEQ ID NO: 30) | CTATGCGCCTTGCCAGCCCGCTCAGATCAGA CACGCACAGGAAACAGCTATGACC |

CGTATCGCCTCCCTCGCGCCA (SEQ ID NO: 13) corresponds to the 5'-adapter known as oligo A that will be adhered to the complementary oligonucleotide in the beads for sequencing.

CTATGCGCCTTGCCAGCCCGC (SEQ ID NO: 14) corresponds to the 5'-adapter known as oligo B that will be adhered to the complementary oligonucleotide in the beads for sequencing.

TCAG corresponds to a key sequence of 4 nucleotides which is identified by the Genome sequencer (GS-Junior or GS-FLX, Roche) during the sequencing process. This key is essential to validate and normalize each sequence during the GS-Junior run.

GTTGTAAAACGACGGCCAGT (SEQ ID NO: 9) corresponds to the fragment sequence of the M13 bacteriophage for the forward primers.

CACAGGAAACAGCTATGACC (SEQ ID NO: 10) corresponds to the fragment sequence of the M13 bacteriophage for reverse primers.

Sequences ACGAGTGCGT (SEQ ID NO: 31), ACGCTCGACA (SEQ ID NO: 32), AGACGCACTC (SEQ ID NO: 33), AGCACTGTAG (SEQ ID NO: 34), and ATCAGACACG (SEQ ID NO: 35) also known as MID for "Molecular Identifiers" are short sequences, validated by the manufacturer (Roche), which are used as a patient's identifier. RT-PCR-Nested amplifications of each patient are mixed in the single-strand library before stating the GS-Junior sequencing run. When finishing the run, a file with a complex mixture of sequences is reported. The MID allows to identify and separate the sequences from each patient. Primers showed in Table 3 correspond to a representative type (5 MIDs) of pairs of primers used for 5 of the analyzed samples. Indeed, 43 different MIDs were used for the 43 different tested samples. These short sequences were provided by the suppliers (Roche) who assures that the 43 MIDs unequivocally identify, without confusion risk, the desired samples to be tested.

The reaction mixture included to a final volume of 50 µl the following ingredients: 5 µl of Buffer (10×), 1 µl (20 µM) of each of the primers (forward and reverse) for amplifying the 5'-UTR-Core or 1.5 µl (20 µM) of each of the degenerate forward and reverse primers, 1 µl (40 µM) dNTP, 2 µl of amplified DNA (5-250 ng), and the corresponding µl of RNase Free Water (Transcriptor one-step RT-PCR Kit, Roche) to a final volume of 50 µl. The mixtures were introduced in the thermo cycler (Applied Biosystems).

Once amplified, the fragments to be further sequenced and corresponding to the spanned 5'-UTR-Core region have generally a minimal length of 446 nucleotides due to the different sequences coupled. In the same way, the fragments to be further sequenced and corresponding to the spanned NS5B region have generally a minimal length of 454 nucleotides due to the different sequences coupled.

All RT-PCR-Nested products, once purified, were mixed (multiplexed) and sequenced following the protocol of the 454 high-throughput sequencing technology, obtaining thousands of sequences (between 60000 and 100000) for each sample. An in-house algorithm (briefly exposed below) was used to demultiplexing the sequenced reads to obtain a separate fasta file with the reads corresponding to each sample and amplicon (patient and HCV region, either 5'-UTR-Core or NS5B). This demultiplexing is carried out by matching corresponding MIDs and primers by alignment with each sequenced read. Hundreds of sequences were obtained for each patient and for each amplicon. Sequences were phylogenetically compared with Sequence References obtained from the GeneBank for subtype classification. This in-house algorithm is capable to detect whether the patient is infected by more than one subtype at the same time. The identification or diagnostic results using the in vitro method of the invention are listed on Table 4 in column identified as GS-Junior.

Briefly, in the algorithm the sequences in a fasta file obtained from the GS-454 Junior were demultiplexed by identifying MID and primer, generating a single fasta file for each sample, region and strand. It followed a quality filter where the sequences having more than a given number of gaps, or more than a given number of Ns (undefined nucleotide A, C, G, T), or more than a given number of differences respect to the dominant haplotype (predominant sequence in the sample) were discarded. For the accepted sequences the remaining gaps and Ns were corrected as per the contents of the dominant haplotype. The reverse complemented (RV) strands were mixed with the forward (FW) strands to obtain a single set of haplotypes and frequencies for each sample and region. An estimate of quasi-species variability was obtained from the full set of haplotypes with corresponding frequencies by means of the Shannon entropy (Sn) and the nucleotidic diversity (Pi). Next there were selected the haplotypes to be used for subtyping. These were the dominant haplotype and all those haplotypes with an identity respect to the dominant haplotype bellow a given threshold, which is region dependent. The selected haplotypes were multiple aligned with the subtypes references of the corresponding region (either 5'-UTR-Core or NS5B). From the multiple alignment and the optimal mutation model of the region there was obtained a matrix of genetic distances between the references and the selected haplotypes for the patient. These distances were then used to build an UPGMA phylogenetic tree, and to estimate the nearest subtype to each of the selected patient haplotypes. A level of confidence was also obtained by means of a bootstrap on the multiple alignment.

Figure 2:
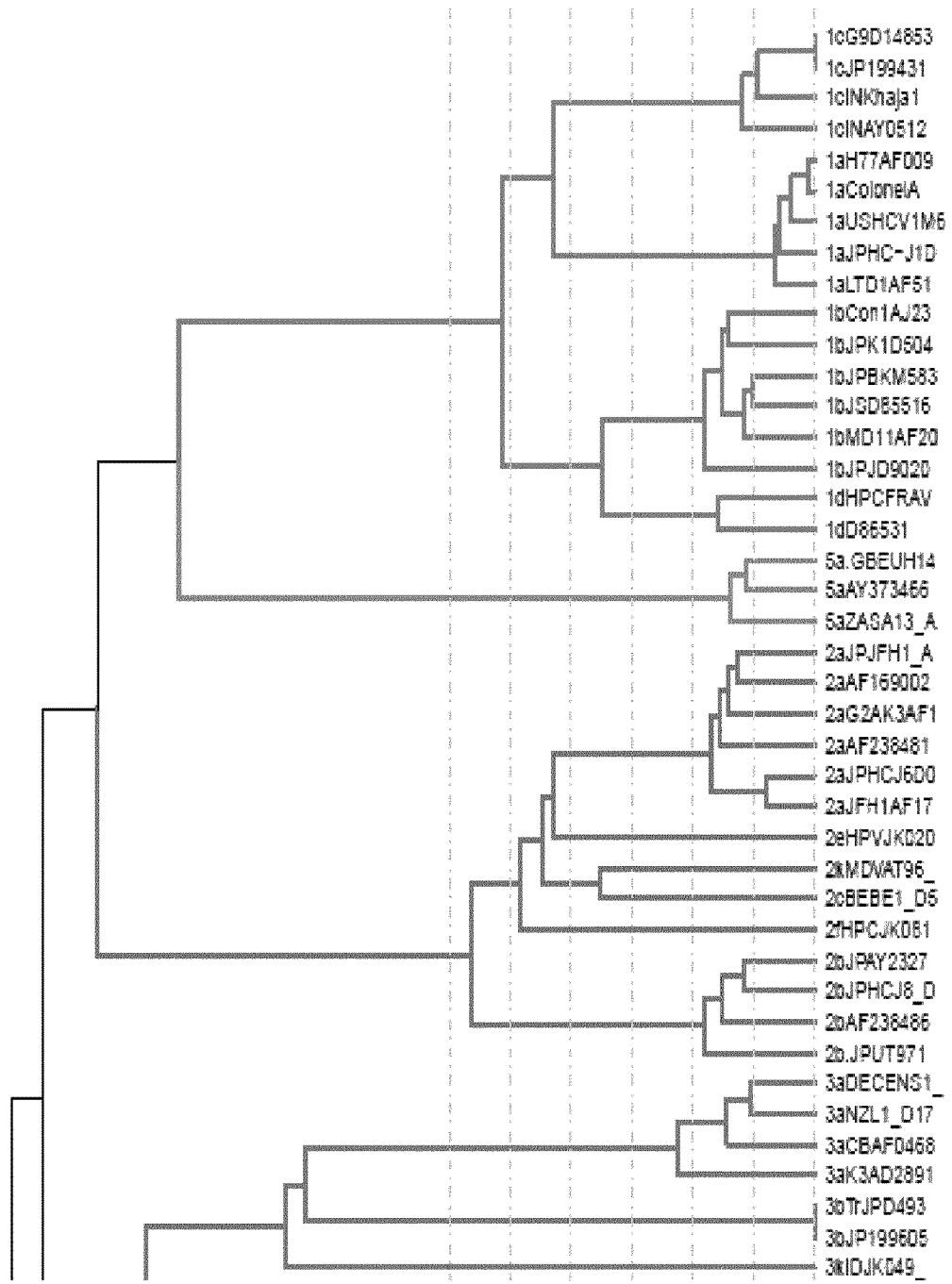
FIG. 2 is also another phylogenetic tree diagram, in which it is emplaced another of the amplified sequences (patient P43, Px1.1506rd) of the tested sample (P43) of the same patient of FIG. 1. In this case, identification of infection with 4d subtype is shown.
Figure 2:
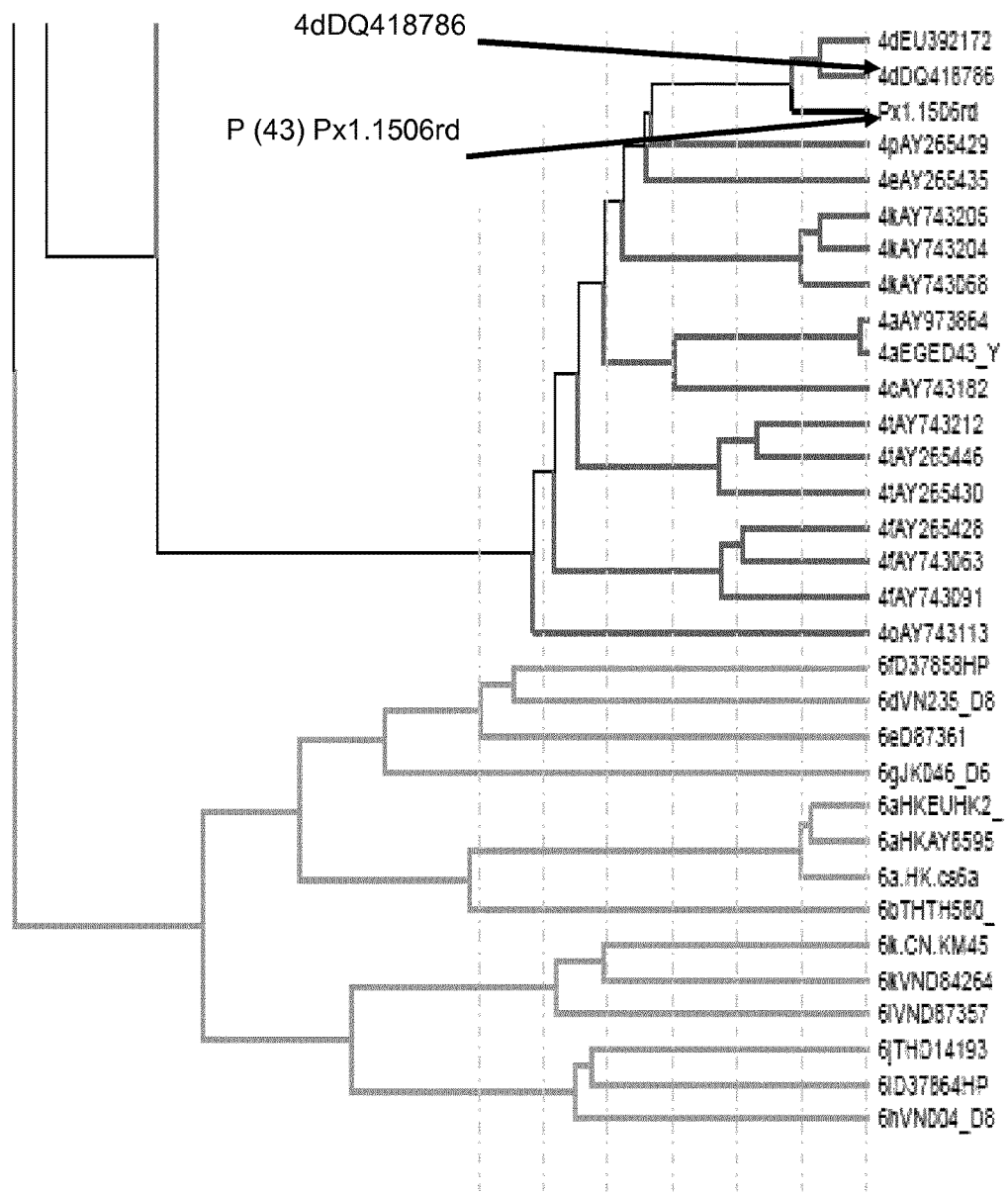

In order to illustrate a mode of out or presentation of the results from the algorithm is shown in FIGS. 1 and 2.

These FIGS. 1 and 2 show, respectively, the diagnostic of the patient of sample 43 (P43). This sample was diagnosed as co-infected by HCV subtypes 4d and 1a. A graphic diagnostic of the infection with subtype 1a is illustrated in FIG. 1 (and its continuation Cont.), wherein the amplified sequence of HCV in the sample P43 (Px10.66rd) is phylogenetically near to subtype 1a (reference 1a LTD1AF51). This correlation is done by determining the distance between subtypes disposed in branches in a phylogenetical tree. In addition, sample 43 also gave rise to the meaningful amplification of another sequence (Px1.1506rd), which well correlated with subtype 4d (reference 4dDQ418786) as can be graphically seen in FIG. 2 (an its continuation Cont.). These type of out or representations allow determining easily the presence of multiple HCV infections in a sample. Each of FIG. 1 and FIG. 2 as a whole shows the entire phylogenetic tree diagram of the different subtypes of HCV. For the purposes of visualization, both figures (FIG. 1 and FIG. 2) have been cut in two parts (partial figures) and are arranged in order the whole figure can be assembled without concealing any part of the partial figures.

1. B) Diagnostic of the 43 samples using Commercial Technique a (CTa; Versant HCV Genotype 2.0, LiPA, Siemens).

This technique is based on a line probe assay (LiPA) targeting both 5'-UTR and core regions of HCV, and was performed following instructions of the commercial product. The result reported by this technique to classify patient 43 is an undetermined result that will need further validation.

1.C) Diagnostic of the 43 samples using Commercial Technique b (CTb; Real Time HCV Genotype II, Abbott).

This technique is based on a real-time PCR targeting NS5B for subtyping 1a and 1b and 5'UTR for the other genotypes. It was performed following instructions of the commercial kit. The result reported by this technique to classify patient 43 is an undetermined result that will need further validation.

1.D) Sanger sequencing is a method of DNA sequencing based on the selective incorporation of chain-terminating dideoxynucleotides by DNA polymerase. We used the Bigdye terminator v1.1 cycle sequencing kit (Applied Biosystems) and a capillar automated DNA-sequencing instrument (Applied Biosystems). The problem of this technique which has been considered the gold standard for HCV classification is that it cannot detect whether a patient is infected with more than one subtype at the same time, and it classify patient 43 as 4d which is the highest represented subtype in the patient.

As above indicated, next Table 4 shows the results of the diagnostic with the four assayed methods in which the Sanger method is used as the reference one.

TABLE 4

Comparative results using the four methods.

| Order | Sanger | CTa | CTb | GS-Junior (invention) |
|---|---|---|---|---|
| 1 | 1a | 1a | 1a | 1a |
| 2 | 1a | 1a | 1a | 1a |
| 3 | 1a | 1a | 1a | 1a |
| 4 | 1b | 1b | 1 | 1b |
| 5 | 1b | 1b | 1b | 1b |
| 6 | 1b | 1b | 1 | 1b |
| 7 | 1b | 1b | 1b | 1b |
| 8 | 1b | 1b | 1b | 1b |
| 9 | 1b | 1b | 1b | 1b |
| 10 | 1b | 1b | 1b | 1b |
| 11 | 2c | 2a/2c | 2 | 2c |
| 12 | 2c | 2a/2c | 2 | 2c |
| 13 | 3a | 3 | 3 | 3a |
| 14 | 3a | 3a | ND | 3a |
| 15 | 3a | 3a | 3 | 3a |
| 16 | 3a | 3a | 3 | 3a |
| 17 | 4a | 4 | 4 | 4a |
| 18 | 4a | 4a/c/d | 4 | 4a |
| 19 | 4d | 4 | 4 | 4d |
| 20 | 4d | 4 | 4 | 4d |
| 21 | 4d | 4a/c/d | 4 | 4d |
| 22 | 4d | 4a/c/d | 4 | 4d |
| 28 | 4f | 4f | 4 + 5 | 4f |
| 29 | 4f | 4f | 4 + 5 | 4f |
| 23 | 4f | 1b + 4f (4 not clear) | 4 + 5 | 4f |
| 24 | 4f | 1b + 4f (4 not clear) | 4 + 5 | 4f |
| 25 | 4f | 1b + 4f (4 not clear) | 4 + 5 | 4f |
| 26 | 4f | 1b + 4f (4 not clear) | 4 + 5 | 4f |
| 27 | 4f | 1b + 4f (4 not clear) | 4 + 5 | 4f |
| 33 | 4f | Und (5, 9, 20) | 4 + 5 | 4f |
| 35 | 4f | Und (5, 9, 16) | 4 + 5 | 4f |
| 30 | 4f | Und (5, 9, 20) | 5 | 4f |
| 31 | 4f | Und (5, 9, 20) | 5 | 4f |
| 32 | 4f | Und (5, 9, 20) | 5 | 4f |
| 34 | 4f | Und (5, 9, 20) | 5 | 4f |
| 36 | 4r | 1 + 4e (not clear) | 1 +4 | 4r |
| 37 | 5a | 5a | 5 | 5a |
| 38 | 6c | neg | 5 | 6c |
| 39 | 2j | 2k | ND | 2j + 4f |
| 40 | 4p | 3a + 4a/c/d | 3 + 4 | 3a + 4p |
| 41 | 4d | 4 | 4 | 4d + 1b |
| 42 | 1a | 1 + 4 | 4 | 4d + 1a |
| 43 | 4d | 1a + 4a/c/d | 1a + 4 | 4d + 1a |

ND means non determined; Und means undetermined; neg. means negativity for amplification.

As can be seen in this Table 4, CTa was able to classify subtypes 1a, 1b, and 3a and 5a, but unable to subtype the rest of genotypes (2, 4 or 6). CTa detected subtypes 4a, 4c and 4d but the report gave an undetermined classification, that was reported as 4 in some cases while 4a/c/d in others. CTa was unable to subtype most of 4f (except case 28, 29), or 6, giving a result of negativity for the genotype 6 in sample 38.

On the other hand, the results using Commercial technique b (CTb) showed that this technique was unable to subtype genotypes 2, 3, 4, 5 or 6. CTb was able to differentiate between subtype 1a and 1 b, but failed in two (samples 4 and 6) out of 7 subtype 1b samples (samples 4-10) that CTb classified as an undefined 1 and in one case it was unable to differentiate between coinfections with 1 b, 1a and 4 (samples 41, 42, and 43). CTb methodology was unable to identify any subtype 4f. Four out of 13 subtypes 4f were classified by CTb as genotype 5 (samples 30, 31, 32, and 34) and the rest were classified as 4 or 5 (4+5) (samples 23, 24, 25, 26, 27, 28, 29, 33, and 35). CTb classified the subtype 4r (sample 36) as an 1 or 4. The subtype 6 was erroneously classified as 5.

Finally, the results with the in vitro method according to the invention (using technology of GS-Junior 454 deep-sequencing platform) revealed that the in vitro method of the invention was able to subtype all 43 samples. GS-Junior (for applying the in vitro method of the invention) detected 5 samples multiple infected (co-infections) with more than one subtype identifying the proportion of each subtype (samples 39, 40, 41, 42 and 43). Thus, the in vitro method of the invention even allowed the detection of multiple infection not usually detectable by the reference method (Sanger), due to the fact that the reference method gives for each analyzed sample an average of the sequences detected.

The final result of the GS-Junior 454 deep-sequencing platform was a Fasta file with hundreds or thousands of sequences able to be used for further studies or future reclassification if required as above detailed.

All these data taken together allow concluding that the in vitro method of the invention is easy to be performed and thus, commercially applicable in form of kits. In addition, the method of the invention allows the fair detection of co-infected samples, as well as the detection of infections with recombinant viruses.

Directly deducible from the results is that the method of the invention is more reliable and sensitive than other commercial techniques in terms that it allows an unequivocally identification of the genotype and subtype of HCV in some complexes samples that cannot be resolved by other techniques. The method of the invention is in addition more precise than the techniques of the prior art, since it not only allows the resolution of multiple infected samples, but also the identification of the subtypes among the multiple genotypes identified in these multiple infected samples.

As indicated along this description, determining the specific variants in HCV infected patients is of great interest to diagnose the patient in a more accurate way because from an accurate diagnosis derives an efficient selected treatment.

In order to illustrate the meaning of an accurate diagnosis, next Example 2 shows the effect of the detected HCV subtype over an specific treatment.

Example 2. Evidences of the Effect of HCV Subtype Over Outcome of the Treatment with Pegylated Interferon and Rivabirin (pegIFN+RBV)

Sustained Virologic Response (SVR) efficacy, which is defined as undetectable serum HCV RNA six months after treatment completion is directly related to the genotype. SVR rates go from 38-41% for genotype 1 (Hadziyannis S J et al. for PEGASYS International Study Group, "Peginterferonalpha 2a and ribavirin combination therapy in chronic hepatitis C: a randomized study of treatment duration and ribavirin dose", Ann Intern Med—2004, vol. 140, pp.: 346-355.), 93% for genotype 2, 79% for genotype 3 (Zeuzem S, et al., "Peginterferon alfa-2b plus ribavirin for treatment of chronic hepatitis C in previously untreated patients infected with HCV genotypes 2 or 3", J Hepatol—2004, vol. 40, pp.: 993-9) and 69% for genotype 4 (Kamal S M et al., "Peginterferon-2b and ribavirin therapy in chronic hepatitis C genotype 4: impact of treatment duration and viral kinetics on sustained virological response. Gut—2005, vol. 54, pp.: 858-66). However, the lack of a highly accurate system to classify patients by the HCV subtype, has impeded to evaluate the response to pegIFN+RBV associated to each particular subtype.

Next Table 5 summarizes the results of a preliminary study of association of subtype with the final outcome after treatment with the standard of care pegIFN+RBV There are some evidences that patients infected with subtype 2b and 4d had particularly low degree of response to peg IFN+RBV. These preliminary data suggest that subtyping may be an important predictive value before starting any treatment in chronic HCV infected patients.

TABLE 5

Study of the association of subtype and response to pegIFN + RBV

| SUB-TYPE | TOTAL number of patients | RESPONSE TO pegIFN + RBV |  |  |  |
|---|---|---|---|---|---|
|  |  | SVR |  | NNR (Null, Bkt o Relapse) |  |
|  |  | Number of Patients | Percentage | Number of Patients | Percentage |
| 1a | 6 | 2 | 33.33% | 4 | 66.67% |
| 1b | 17 | 8 | 47.06% | 9 | 52.94% |
| 2b | 2 | 0 | 0.00% | 2 | 100.00% |
| 2c | 5 | 3 | 60.00% | 2 | 40.00% |
| 3a | 8 | 6 | 75.00% | 2 | 25.00% |
| 4a | 2 | 1 | 50.00% | 1 | 50.00% |
| 4d | 6 | 1 | 16.67% | 5 | 83.33% |

NR means No response. This kind of NR can be of different types: a) Null, when from the start of the treatment viral load does not low; Break through (Bkt) when at initial stages of the treatment the viral load is diminished but appears next; and Relapse, when viral load is eliminated (or lowered to very small undetectable amounts) within the treatment but after leaving said treatment, viral load newly appears approximately 6 months later on stopping treatment.

Therefore, with the aim of solving costs and time (really important for the patients), it is highly envisaged to accurately identify the HCV variant genotype and subtype in an infected isolated sample. The method of the invention, using the specific oligonucleotides for spanning the key HCV meaningful and distinguishing variant regions, is conceived as a valuable tool to carry out this aim.

REFERENCES CITED IN THE APPLICATION

Simmonds et al., "Consensus proposals for a unified system of nomenclature of hepatitis C virus genotypes", Hepatology—2005, vol. 42, pp. 963-973.

Chevaliez S. et. al. "Hepatitis C virus (HCV) genotype 1 subtype identification in new HCV drug development and future clinical practice", PLoS ONE, 2009, vol. 4, pp. 1-9.

Kuiken et al., "A Comprehensive System for Consistent Numbering of HCV Sequences, Proteins and Epitopes", *Hepatology*—2006, DOI 10.1002/hep.21377, pp. 1355-1361.

Lauck M., et. al. "Analysis of hepatitis C virus intra-host diversity across the coding region by ultra-deep sequencing". *J. Virol.*—2012, Epub (online publication, ahead of print).

Hadziyannis S J et al. for PEGASYS International Study Group, "Peginterferonalpha 2a and ribavirin combination therapy in chronic hepatitis C: a randomized study of treatment duration and ribavirin dose", *Ann Intern Med*—2004, vol. 140, pp.: 346-355.

Zeuzem S, et al., "Peginterferon alfa-2b plus ribavirin for treatment of chronic hepatitis C in previously untreated patients infected with HCV genotypes 2 or 3", *J Hepatol*—2004, vol. 40, pp.: 993-9.

Kamal S M et al., "Peginterferon-2b and ribavirin therapy in chronic hepatitis C genotype 4: impact of treatment duration and viral kinetics on sustained virological response. *Gut*—2005, vol. 54, pp.: 858-66.

---

The invention claimed is:

1. An in vitro method for determining in an isolated sample of a subject the presence of one or more Human Hepatitis C Virus (HCV) sequence variants comprising:
   i) reverse transcribing and amplifying HCV RNAs molecules by reverse transcription polymerase chain reaction (RT-PCR) using
   a set of primers comprising the oligonucleotide of formula (I), (N)m-Z (I), as a reverse primer, wherein Z is an oligonucleotide consisting of SEQ ID NO: 1 (5'-CTAGTCGCGCGCACACCCA-3'),
   m is an integer ranging from 0 to 25 nucleotides, and N is a nucleotide selected from Adenine, Thymine, Cytosine, or Guanine; and a forward primer capable of hybridizing to the 5'-UTR-Core portion of HCV, wherein the set of primers is capable of generating a fragment comprising a portion of the HCV genome corresponding to nucleotide position numbers 45 to 490 of SEQ ID NO: 2; and
   a set of primers comprising the oligonucleotide of formula (II), (N)m-F (II), as a reverse primer, wherein F is an oligonucleotide consisting of SEQ ID NO: 5 (5'-TTNGADGAGCADGATGTWATBAGCTC-3'), in which N means Adenine (A), Cytosine (C), Guanine (G) or Thymine (T); D means G, A or T; W means A or T, B means G, T or C, and
   m is an integer ranging from 0 to 25 nucleotides; and a forward primer capable of hybridizing to the NS5B portion of HCV, wherein the set of primers is capable of generating a fragment comprising a portion of the HCV genome corresponding to nucleotide position numbers 653 to 1106 of SEQ ID NO: 6;
   ii) further amplifying the fragments generated in step i) by PCR using
   a set of primers comprising the oligonucleotide of formula (I) as a reverse primer, and a forward primer capable of hybridizing to the 5'-UTR-Core portion of HCV, wherein the set of primers is capable of generating a fragment comprising a portion of the HCV genome corresponding to nucleotide position numbers 146 to 490 of SEQ ID NO: 2; and
   a set of primers comprising the oligonucleotide consisting of SEQ ID NO: 7 as a forward primer, and a reverse primer capable of hybridizing to the NS5B portion of HCV, wherein the set of primers is capable of generating a fragment comprising a portion of the HCV genome corresponding to nucleotide position numbers 653 to 1040 of SEQ ID NO: 6, and
   iii) sequencing the amplified fragments obtained in step ii).

2. The method of claim 1, wherein in step i) reverse transcribing and amplifying HCV RNAs molecules is performed using
   a set of primers wherein the forward primer consists of SEQ ID NO: 3 and the oligonucleotide of formula (I) is the reverse primer, and
   a set of primers comprising the oligonucleotide of formula (II) as a reverse primer, and wherein the forward primer consists of SEQ ID NO: 7.

3. The method according to claim 1, wherein step ii) is performed using
   a set of primers in which the forward primer consists of SEQ ID NO: 4 and the oligonucleotide of formula (I) is the reverse primer, and
   a set of primers comprising the oligonucleotide consisting of SEQ ID NO: 7 as a forward primer and wherein the reverse primer consists of SEQ ID NO: 8.

4. The method according to claim 2, wherein step ii) is performed using
   a set of primers, in which the forward primer consists of SEQ ID NO: 4 and the oligonucleotide of formula (I) is the reverse primer, and
   a set of primers comprising the oligonucleotide consisting of SEQ ID NO: 7 as a forward primer and wherein the reverse primer consists of SEQ ID NO: 8.

* * * * *

SEQUENCE LISTING

<160> NUMBER OF SEQ ID NOS: 73

<210> SEQ ID NO 1
<211> LENGTH: 19
<212> TYPE: DNA
<213> ORGANISM: Artificial
<220> FEATURE:
<223> OTHER INFORMATION: Reverse primer

<400> SEQUENCE: 1
ctagtcgcgc gcacaccca                     19

<210> SEQ ID NO 2
<211> LENGTH: 914
<212> TYPE: DNA
<213> ORGANISM: Hepatitis C virus

<400> SEQUENCE: 2
gccagccccc tgatgggggc gacactccac catgaatcac tccctgtga ggaactactg      60 tcttcacgca gaaagcgtct agccatggcg ttagtatgag tgtcgtgcag cctccaggac     120 ccccctccc gggagagcca tagtggtctg cggaaccggt gagtacaccg gaattgccag     180
gacgaccggg tcctttcttg gataaacccg ctcaatgcct ggagatttgg gcgtgccccc     240
gcaagactgc tagccgagta gtgttgggtc gcgaaaggcc ttgtggtact gcctgatagg     300
gtgcttgcga gtgccccggg aggtctcgta gaccgtgcac catgagcacg aatcctaaac     360
ctcaaagaaa aaccaaacgt aacaccaacc gtcgcccaca ggacgtcaag ttcccgggtg     420
gcggtcagat cgttggtgga gtttacttgt tgccgcgcag gggccctaga ttgggtgtgc     480
gcgcgacgag gaagacttcc gagcggtcgc aacctcgagg tagacgtcag cctatcccca     540
aggcacgtcg gcccgagggc aggacctggg ctcagcccgg gtacccttgg cccctctatg     600
gcaatgaggg ttgcgggtgg gcgggatggc tcctgtctcc ccgtggctct cggcctagct     660
ggggccccac agaccccgg cgtaggtcgc gcaatttggg taaggtcatc gatacccta      720 cgtgcggctt cgccgacctc atggggtaca taccgctcgt cggcgcccct cttggaggcg     780
ctgccagggc cctggcgcat ggcgtccggg ttctggaaga cggcgtgaac tatgcaacag     840
ggaaccttcc tggttgctct ttctctatct tccttctggc cctgctctct tgcctgactg     900
tgcccgcttc agcc                         914

<210> SEQ ID NO 3
<211> LENGTH: 27
<212> TYPE: DNA
<213> ORGANISM: Artificial
<220> FEATURE:
<223> OTHER INFORMATION: Forward primer

<400> SEQUENCE: 3
ctgtgaggaa ctactgtctt cacgcag             27

```
<210> SEQ ID NO 4
<211> LENGTH: 22
<212> TYPE: DNA
<213> ORGANISM: Artificial
<220> FEATURE:
<223> OTHER INFORMATION: Forward primer

<400> SEQUENCE: 4
gtctgcggaa ccggtgagta ca                                            22

<210> SEQ ID NO 5
<211> LENGTH: 26
<212> TYPE: DNA
<213> ORGANISM: Artificial
<220> FEATURE:
<223> OTHER INFORMATION: Reverse primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: D means G, A or T
<220> FEATURE:
<221> NAME/KEY: misc_feature
<222> LOCATION: (12)..(12)
<223> OTHER INFORMATION: D means G, A or T
<220> FEATURE:
<221> NAME/KEY: misc_feature
<222> LOCATION: (18)..(18)
<223> OTHER INFORMATION: W means  A or T
<220> FEATURE:
<221> NAME/KEY: misc_feature
<222> LOCATION: (21)..(21)
<223> OTHER INFORMATION: B means G, T or C

<400> SEQUENCE: 5
ttngadgagc adgatgtwat bagctc                                        26

<210> SEQ ID NO 6
<211> LENGTH: 1776
<212> TYPE: DNA
<213> ORGANISM: Hepatitis C virus

<400> SEQUENCE: 6
tcaatgtctt attcctggac aggcgcactc gtcaccccgt gcgctgcgga agaacaaaaa    60
ctgcccatca acgcactgag caactcgttg ctacgccatc acaatctggt gtattccacc   120
acttcacgca gtgcttgcca aaggcagaag aaagtcacat tgacagact gcaagttctg   180 gacagccatt accaggacgt gctcaaggag gtcaaagcag cggcgtcaaa agtgaaggct   240
aacttgctat ccgtagagga agcttgcagc ctgacgcccc acattcagc caaatccaag   300 tttggctatg gggcaaaaga cgtccgttgc catgccagaa aggccgtagc ccacatcaac   360
tccgtgtgga aagaccttct ggaagacagt gtaacaccaa tagacactac catcatggcc   420
aagaacgagg tttctgcgt tcagcctgag aaggggggtc gtaagccagc tcgtctcatc   480
gtgttccccg acctgggcgt gcgcgtgtgc gagaagatgg ccctgtacga cgtggttagc   540
aagctccccc tggccgtgat gggaagctcc tacggattcc aatactcacc aggacagcgg   600
gttgaattcc tcgtgcaagc gtggaagtcc aagaagaccc cgatgggggtt ctcgtatgat   660 acccgctgtt ttgactccac agtcactgag agcgacatcc gtacggagga ggcaatttac   720
caatgttgtg acctggaccc ccaagcccgc gtggccatca gtcccctcac tgagaggctt   780
tatgttgggg gccctcttac caattcaagg ggggaaaact gcggctaccg caggtgccgc   840
```

```
gcgagcggcg tactgacaac tagctgtggt aacaccctca cttgctacat caaggcccgg      900
gcagcctgtc gagccgcagg gctccaggac tgcaccatgc tcgtgtgtgg cgacgactta      960
gtcgttatct gtgaaagtgc gggggtccag gaggacgcgg cgagcctgag agccttcacg     1020
gaggctatga ccaggtactc cgccccccc ggggacccc cacaaccaga atacgacttg       1080
gagcttataa catcatgctc ctccaacgtg tcagtcgccc acgacggcgc tggaaagagg     1140
gtctactacc ttacccgtga ccctacaacc cccctcgcga gagccgcgtg ggagacagca     1200
agacacactc cagtcaattc ctggctaggc aacataatca tgtttgcccc cacactgtgg     1260
gcgaggatga tactgatgac ccatttcttt agcgtcctca tagccaggga tcagcttgaa     1320
caggctctta actgtgagat ctacggagcc tgctactcca tagaaccact ggatctacct     1380
ccaatcattc aaagactcca tggcctcagc gcattttcac tccacagtta ctctccaggt     1440
gaaatcaata gggtggccgc atgcctcaga aaacttgggg tcccgccctt gcgagcttgg     1500
agacaccggg cccggagcgt ccgcgctagg cttctgtcca gaggaggcag gctgccata     1560 tgtggcaagt acctcttcaa ctgggcagta agaacaaagc tcaaactcac tccaatagcg     1620
gccgctggcc ggctggactt gtccggttgg ttcacggctg gctacagcgg gggagacatt     1680
tatcacagcg tgtctcatgc ccggccccgc tggttctggt tttgcctact cctgctcgct     1740 gcagggtag gcatctacct cctccccaac cgatga                                1776
```

```
<210> SEQ ID NO 7
<211> LENGTH: 25
<212> TYPE: DNA
<213> ORGANISM: Artificial
<220> FEATURE:
<223> OTHER INFORMATION: Forward primer
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(5)
<223> OTHER INFORMATION: Y means T or C
<220> FEATURE:
<221> NAME/KEY: misc_feature
<222> LOCATION: (8)..(8)
<223> OTHER INFORMATION: Y means T or C
<220> FEATURE:
<221> NAME/KEY: misc_feature
<222> LOCATION: (12)..(12)
<223> OTHER INFORMATION: M means A or C
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (17)..(17)
<223> OTHER INFORMATION: Y means T or C

<400> SEQUENCE: 7
cntaygayac cmgntgyttt gactc                                            25

<210> SEQ ID NO 8
<211> LENGTH: 26
<212> TYPE: DNA
<213> ORGANISM: Artificial
<220> FEATURE:
<223> OTHER INFORMATION: Reverse primer
<220> FEATURE:
<221> NAME/KEY: misc_feature
<222> LOCATION: (3)..(3)
<223> OTHER INFORMATION: R means G or A
```

```
<220> FEATURE:
<221> NAME/KEY: misc_feature
<222> LOCATION: (6)..(6)
<223> OTHER INFORMATION: Y means T or C
<220> FEATURE:
<221> NAME/KEY: misc_feature
<222> LOCATION: (18)..(18)
<223> OTHER INFORMATION: n is a, c, g, or t

<400> SEQUENCE: 8
gartayctgg tcatagcntc cgtgaa                                              26

<210> SEQ ID NO 9
<211> LENGTH: 20
<212> TYPE: DNA
<213> ORGANISM: Bacteriophage M13

<400> SEQUENCE: 9
gttgtaaaac gacggccagt                                                    20

<210> SEQ ID NO 10
<211> LENGTH: 20
<212> TYPE: DNA
<213> ORGANISM: Bacteriophage M13

<400> SEQUENCE: 10
cacaggaaac agctatgacc                                                    20

<210> SEQ ID NO 11
<211> LENGTH: 41
<212> TYPE: DNA
<213> ORGANISM: Artificial
<220> FEATURE:
<223> OTHER INFORMATION: Fragment of a forward primer including a
      fragment of bacteriophage M13 + universal oligo A adapter for
      454-pyrosequencing technology

<400> SEQUENCE: 11
cgtatcgcct ccctcgcgcc agttgtaaaa cgacggccag t                            41

<210> SEQ ID NO 12
<211> LENGTH: 41
<212> TYPE: DNA
<213> ORGANISM: Artificial
<220> FEATURE:
<223> OTHER INFORMATION: Fragment of a reverse primer including a
      fragment of bacteriophage M3 + universal oligo B adapter for
      454-pyrosequencing technology

<400> SEQUENCE: 12
ctatgcgcct tgccagcccg ccacaggaaa cagctatgac c                            41

<210> SEQ ID NO 13
<211> LENGTH: 21
<212> TYPE: DNA
<213> ORGANISM: Artificial
<220> FEATURE:
<223> OTHER INFORMATION: oligo A adapter for forward primers in the
      454-pyrosequence technology

<400> SEQUENCE: 13
cgtatcgcct ccctcgcgcc a                                                  21

<210> SEQ ID NO 14
<211> LENGTH: 21
<212> TYPE: DNA
<213> ORGANISM: Artificial
```

<220> FEATURE:
<223> OTHER INFORMATION: oligo B adapter for reverse primers in the
      454-pyrosequencing technology

<400> SEQUENCE: 14
ctatgcgcct tgccagcccg c                                              21

<210> SEQ ID NO 15
<211> LENGTH: 20
<212> TYPE: DNA
<213> ORGANISM: Artificial
<220> FEATURE:
<223> OTHER INFORMATION: Reverse primer
<220> FEATURE:
<221> NAME/KEY: misc_feature
<222> LOCATION: (1)..(1)
<223> OTHER INFORMATION: N means (N)m, wherein N is any nucleotide
      selected from A, T, C or G, and m is an integer from 0 to 25

<400> SEQUENCE: 15
nctagtcgcg cgcacaccca                                                20

<210> SEQ ID NO 16
<211> LENGTH: 27
<212> TYPE: DNA
<213> ORGANISM: Artificial
<220> FEATURE:
<223> OTHER INFORMATION: Reverse primer
<220> FEATURE:
<221> NAME/KEY: misc_feature
<222> LOCATION: (1)..(1)
<223> OTHER INFORMATION: N means (N)m, wherein N is any nucleotide
      selected from A, T, C or G, and m is an integer from 0 to 25
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (7)..(7)
<223> OTHER INFORMATION: D means G, A or T
<220> FEATURE:
<221> NAME/KEY: misc_feature
<222> LOCATION: (13)..(13)
<223> OTHER INFORMATION: D means G, A or T
<220> FEATURE:
<221> NAME/KEY: misc_feature
<222> LOCATION: (19)..(19)
<223> OTHER INFORMATION: W means A or T
<220> FEATURE:
<221> NAME/KEY: misc_feature
<222> LOCATION: (22)..(22)
<223> OTHER INFORMATION: B means G, T or C

<400> SEQUENCE: 16
nttngadgag cadgatgtwa tbagctc                                        27

<210> SEQ ID NO 17
<211> LENGTH: 42
<212> TYPE: DNA
<213> ORGANISM: Artificial
<220> FEATURE:
<223> OTHER INFORMATION: Forward primer

<400> SEQUENCE: 17
gttgtaaaac gacggccagt gtctgcggaa ccggtgagta ca                       42

<210> SEQ ID NO 18
<211> LENGTH: 39
<212> TYPE: DNA
<213> ORGANISM: Artificial

```
<220> FEATURE:
<223> OTHER INFORMATION: Reverse primer

<400> SEQUENCE: 18
cacaggaaac agctatgacc ctagtcgcgc gcacaccca                    39

<210> SEQ ID NO 19
<211> LENGTH: 45
<212> TYPE: DNA
<213> ORGANISM: Artificial
<220> FEATURE:
<223> OTHER INFORMATION: Forward primer
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: Y means T or C
<220> FEATURE:
<221> NAME/KEY: misc_feature
<222> LOCATION: (28)..(28)
<223> OTHER INFORMATION: Y means T or C
<220> FEATURE:
<221> NAME/KEY: misc_feature
<222> LOCATION: (32)..(32)
<223> OTHER INFORMATION: M means A or C
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (37)..(37)
<223> OTHER INFORMATION: Y means T or C

<400> SEQUENCE: 19
gttgtaaaac gacggccagt cntaygayac cmgntgyttt gactc            45

<210> SEQ ID NO 20
<211> LENGTH: 46
<212> TYPE: DNA
<213> ORGANISM: Artificial
<220> FEATURE:
<223> OTHER INFORMATION: Reverse primer
<220> FEATURE:
<221> NAME/KEY: misc_feature
<222> LOCATION: (23)..(23)
<223> OTHER INFORMATION: R means A or G
<220> FEATURE:
<221> NAME/KEY: misc_feature
<222> LOCATION: (26)..(26)
<223> OTHER INFORMATION: Y means T or C
<220> FEATURE:
<221> NAME/KEY: misc_feature
<222> LOCATION: (38)..(38)
<223> OTHER INFORMATION: N means A, C, G or T

<400> SEQUENCE: 20
cacaggaaac agctatgacc gartayctgg tcatagcntc cgtgaa           46

<210> SEQ ID NO 21
<211> LENGTH: 55
<212> TYPE: DNA
<213> ORGANISM: Artificial
<220> FEATURE:
<223> OTHER INFORMATION: Forward primer

<400> SEQUENCE: 21
cgtatcgcct ccctcgcgcc atcagacgag tgcgtgttgt aaaacgacgg ccagt  55
```

<210> SEQ ID NO 22
<211> LENGTH: 55
<212> TYPE: DNA
<213> ORGANISM: Artificial
<220> FEATURE:
<223> OTHER INFORMATION: Reverse primer

<400> SEQUENCE: 22
ctatgcgcct tgccagcccg ctcagacgag tgcgtcacag gaaacagcta tgacc        55

<210> SEQ ID NO 23
<211> LENGTH: 55
<212> TYPE: DNA
<213> ORGANISM: Artificial
<220> FEATURE:
<223> OTHER INFORMATION: Forward primer

<400> SEQUENCE: 23
cgtatcgcct ccctcgcgcc atcagacgct cgacagttgt aaaacgacgg ccagt        55

<210> SEQ ID NO 24
<211> LENGTH: 55
<212> TYPE: DNA
<213> ORGANISM: Artificial
<220> FEATURE:
<223> OTHER INFORMATION: Reverse primer

<400> SEQUENCE: 24
ctatgcgcct tgccagcccg ctcagacgct cgacacacag gaaacagcta tgacc        55

<210> SEQ ID NO 25
<211> LENGTH: 55
<212> TYPE: DNA
<213> ORGANISM: Artificial
<220> FEATURE:
<223> OTHER INFORMATION: Forward primer

<400> SEQUENCE: 25
cgtatcgcct ccctcgcgcc atcagagacg cactcgttgt aaaacgacgg ccagt        55

<210> SEQ ID NO 26
<211> LENGTH: 55
<212> TYPE: DNA
<213> ORGANISM: Artificial
<220> FEATURE:
<223> OTHER INFORMATION: Reverse primer

<400> SEQUENCE: 26
ctatgcgcct tgccagcccg ctcagagacg cactccacag gaaacagcta tgacc        55

<210> SEQ ID NO 27
<211> LENGTH: 55
<212> TYPE: DNA
<213> ORGANISM: Artificial
<220> FEATURE:
<223> OTHER INFORMATION: Forward primer

<400> SEQUENCE: 27
cgtatcgcct ccctcgcgcc atcagagcac tgtaggttgt aaaacgacgg ccagt        55

<210> SEQ ID NO 28
<211> LENGTH: 55
<212> TYPE: DNA
<213> ORGANISM: Artificial
<220> FEATURE:
<223> OTHER INFORMATION: Reverse primer

<400> SEQUENCE: 28
ctatgcgcct tgccagcccg ctcagagcac tgtagcacag gaaacagcta tgacc    55

<210> SEQ ID NO 29
<211> LENGTH: 55
<212> TYPE: DNA
<213> ORGANISM: Artificial
<220> FEATURE:
<223> OTHER INFORMATION: Forward primer

<400> SEQUENCE: 29
cgtatcgcct ccctcgcgcc atcagatcag acacggttgt aaaacgacgg ccagt    55

<210> SEQ ID NO 30
<211> LENGTH: 55
<212> TYPE: DNA
<213> ORGANISM: Artificial
<220> FEATURE:
<223> OTHER INFORMATION: Reverse primer

<400> SEQUENCE: 30
ctatgcgcct tgccagcccg ctcagatcag acacgcacag gaaacagcta tgacc    55

<210> SEQ ID NO 31
<211> LENGTH: 10
<212> TYPE: DNA
<213> ORGANISM: Artificial
<220> FEATURE:
<223> OTHER INFORMATION: Molecular identifier

<400> SEQUENCE: 31
acgagtgcgt    10

<210> SEQ ID NO 32
<211> LENGTH: 10
<212> TYPE: DNA
<213> ORGANISM: Artificial
<220> FEATURE:
<223> OTHER INFORMATION: Molecular identifier

<400> SEQUENCE: 32
acgctcgaca    10

<210> SEQ ID NO 33
<211> LENGTH: 10
<212> TYPE: DNA
<213> ORGANISM: Artificial
<220> FEATURE:
<223> OTHER INFORMATION: Molecular identifier

<400> SEQUENCE: 33
agacgcactc    10

<210> SEQ ID NO 34
<211> LENGTH: 10
<212> TYPE: DNA
<213> ORGANISM: Artificial
<220> FEATURE:
<223> OTHER INFORMATION: Molecular identifier

<400> SEQUENCE: 34
agcactgtag    10

```
<210> SEQ ID NO 35
<211> LENGTH: 10
<212> TYPE: DNA
<213> ORGANISM: Artificial
<220> FEATURE:
<223> OTHER INFORMATION: Molecular identifier

<400> SEQUENCE: 35
atcagacacg                                                              10

<210> SEQ ID NO 36
<211> LENGTH: 26
<212> TYPE: DNA
<213> ORGANISM: Artificial
<220> FEATURE:
<223> OTHER INFORMATION: Reverse primer

<400> SEQUENCE: 36
ttagatgagc atgatgtaat gagctc                                            26

<210> SEQ ID NO 37
<211> LENGTH: 26
<212> TYPE: DNA
<213> ORGANISM: Artificial
<220> FEATURE:
<223> OTHER INFORMATION: Reverse primer

<400> SEQUENCE: 37
ttagatgagc atgatgtaat tagctc                                            26

<210> SEQ ID NO 38
<211> LENGTH: 26
<212> TYPE: DNA
<213> ORGANISM: Artificial
<220> FEATURE:
<223> OTHER INFORMATION: Reverse primer

<400> SEQUENCE: 38
ttagatgagc atgatgtaat cagctc                                            26

<210> SEQ ID NO 39
<211> LENGTH: 26
<212> TYPE: DNA
<213> ORGANISM: Artificial
<220> FEATURE:
<223> OTHER INFORMATION: Reverse primer

<400> SEQUENCE: 39
ttagatgagc atgatgttat gagctc                                            26

<210> SEQ ID NO 40
<211> LENGTH: 26
<212> TYPE: DNA
<213> ORGANISM: Artificial
<220> FEATURE:
<223> OTHER INFORMATION: Reverse primer

<400> SEQUENCE: 40
ttagatgagc atgatgttat tagctc                                            26

<210> SEQ ID NO 41
<211> LENGTH: 26
<212> TYPE: DNA
<213> ORGANISM: Artificial
<220> FEATURE:
<223> OTHER INFORMATION: Reverse primer
```

```
<400> SEQUENCE: 41
ttagatgagc atgatgttat cagctc                                        26

<210> SEQ ID NO 42
<211> LENGTH: 26
<212> TYPE: DNA
<213> ORGANISM: Artificial
<220> FEATURE:
<223> OTHER INFORMATION: Reverse primer

<400> SEQUENCE: 42
ttagatgagc aggatgtaat gagctc                                        26

<210> SEQ ID NO 43
<211> LENGTH: 26
<212> TYPE: DNA
<213> ORGANISM: Artificial
<220> FEATURE:
<223> OTHER INFORMATION: Reverse primer

<400> SEQUENCE: 43
ttagatgagc aggatgtaat tagctc                                        26

<210> SEQ ID NO 44
<211> LENGTH: 26
<212> TYPE: DNA
<213> ORGANISM: Artificial
<220> FEATURE:
<223> OTHER INFORMATION: Reverse primer

<400> SEQUENCE: 44
ttagatgagc aggatgtaat cagctc                                        26

<210> SEQ ID NO 45
<211> LENGTH: 26
<212> TYPE: DNA
<213> ORGANISM: Artificial
<220> FEATURE:
<223> OTHER INFORMATION: Reverse primer

<400> SEQUENCE: 45
ttagatgagc aggatgttat gagctc                                        26

<210> SEQ ID NO 46
<211> LENGTH: 26
<212> TYPE: DNA
<213> ORGANISM: Artificial
<220> FEATURE:
<223> OTHER INFORMATION: Reverse primer

<400> SEQUENCE: 46
ttagatgagc aggatgttat tagctc                                        26

<210> SEQ ID NO 47
<211> LENGTH: 26
<212> TYPE: DNA
<213> ORGANISM: Artificial
<220> FEATURE:
<223> OTHER INFORMATION: Reverse primer

<400> SEQUENCE: 47
ttagatgagc aggatgttat cagctc                                        26
```

```
<210> SEQ ID NO 48
<211> LENGTH: 26
<212> TYPE: DNA
<213> ORGANISM: Artificial
<220> FEATURE:
<223> OTHER INFORMATION: Reverse primer

<400> SEQUENCE: 48
ttagatgagc aagatgtaat gagctc                                           26

<210> SEQ ID NO 49
<211> LENGTH: 26
<212> TYPE: DNA
<213> ORGANISM: Artificial
<220> FEATURE:
<223> OTHER INFORMATION: Reverse primer

<400> SEQUENCE: 49
ttagatgagc aagatgtaat tagctc                                           26

<210> SEQ ID NO 50
<211> LENGTH: 26
<212> TYPE: DNA
<213> ORGANISM: Artificial
<220> FEATURE:
<223> OTHER INFORMATION: Reverse primer

<400> SEQUENCE: 50
ttagatgagc aagatgtaat cagctc                                           26

<210> SEQ ID NO 51
<211> LENGTH: 26
<212> TYPE: DNA
<213> ORGANISM: Artificial
<220> FEATURE:
<223> OTHER INFORMATION: Reverse primer

<400> SEQUENCE: 51
ttagatgagc aagatgttat gagctc                                           26

<210> SEQ ID NO 52
<211> LENGTH: 26
<212> TYPE: DNA
<213> ORGANISM: Artificial
<220> FEATURE:
<223> OTHER INFORMATION: Reverse primer

<400> SEQUENCE: 52
ttagatgagc aagatgttat tagctc                                           26

<210> SEQ ID NO 53
<211> LENGTH: 26
<212> TYPE: DNA
<213> ORGANISM: Artificial
<220> FEATURE:
<223> OTHER INFORMATION: Reverse primer

<400> SEQUENCE: 53
ttagatgagc aagatgttat cagctc                                           26

<210> SEQ ID NO 54
<211> LENGTH: 25
<212> TYPE: DNA
<213> ORGANISM: Artificial
<220> FEATURE:
<223> OTHER INFORMATION: Forward primer
```

```
<400> SEQUENCE: 54
catatgatac cagatgcttt gactc                                              25

<210> SEQ ID NO 55
<211> LENGTH: 25
<212> TYPE: DNA
<213> ORGANISM: Artificial
<220> FEATURE:
<223> OTHER INFORMATION: Forward primer

<400> SEQUENCE: 55
catatgatac cagatgtttt gactc                                              25

<210> SEQ ID NO 56
<211> LENGTH: 25
<212> TYPE: DNA
<213> ORGANISM: Artificial
<220> FEATURE:
<223> OTHER INFORMATION: Forward primer

<400> SEQUENCE: 56
catatgatac cagttgcttt gactc                                              25

<210> SEQ ID NO 57
<211> LENGTH: 25
<212> TYPE: DNA
<213> ORGANISM: Artificial
<220> FEATURE:
<223> OTHER INFORMATION: Forward primer

<400> SEQUENCE: 57
catatgatac cagttgtttt gactc                                              25

<210> SEQ ID NO 58
<211> LENGTH: 25
<212> TYPE: DNA
<213> ORGANISM: Artificial
<220> FEATURE:
<223> OTHER INFORMATION: Forward primer

<400> SEQUENCE: 58
catatgatac caggtgcttt gactc                                              25

<210> SEQ ID NO 59
<211> LENGTH: 25
<212> TYPE: DNA
<213> ORGANISM: Artificial
<220> FEATURE:
<223> OTHER INFORMATION: Forward primer

<400> SEQUENCE: 59
catatgatac caggtgtttt gactc                                              25

<210> SEQ ID NO 60
<211> LENGTH: 25
<212> TYPE: DNA
<213> ORGANISM: Artificial
<220> FEATURE:
<223> OTHER INFORMATION: Forward primer

<400> SEQUENCE: 60
catatgatac cagctgcttt gactc                                              25
```

```
<210> SEQ ID NO 61
<211> LENGTH: 25
<212> TYPE: DNA
<213> ORGANISM: Artificial
<220> FEATURE:
<223> OTHER INFORMATION: Forward primer

<400> SEQUENCE: 61
catatgatac cagctgtttt gactc                                         25

<210> SEQ ID NO 62
<211> LENGTH: 25
<212> TYPE: DNA
<213> ORGANISM: Artificial
<220> FEATURE:
<223> OTHER INFORMATION: Forward primer

<400> SEQUENCE: 62
catatgatac ccgatgcttt gactc                                         25

<210> SEQ ID NO 63
<211> LENGTH: 25
<212> TYPE: DNA
<213> ORGANISM: Artificial
<220> FEATURE:
<223> OTHER INFORMATION: Forward primer

<400> SEQUENCE: 63
catatgatac ccgatgtttt gactc                                         25

<210> SEQ ID NO 64
<211> LENGTH: 25
<212> TYPE: DNA
<213> ORGANISM: Artificial
<220> FEATURE:
<223> OTHER INFORMATION: Forward primer

<400> SEQUENCE: 64
catatgatac ccgttgcttt gactc                                         25

<210> SEQ ID NO 65
<211> LENGTH: 25
<212> TYPE: DNA
<213> ORGANISM: Artificial
<220> FEATURE:
<223> OTHER INFORMATION: Forward primer

<400> SEQUENCE: 65
catatgatac ccgttgtttt gactc                                         25

<210> SEQ ID NO 66
<211> LENGTH: 25
<212> TYPE: DNA
<213> ORGANISM: Artificial
<220> FEATURE:
<223> OTHER INFORMATION: Forward primer

<400> SEQUENCE: 66
catatgatac ccggtgcttt gactc                                         25

<210> SEQ ID NO 67
<211> LENGTH: 25
<212> TYPE: DNA
<213> ORGANISM: Artificial
<220> FEATURE:
<223> OTHER INFORMATION: Forward primer
```

```
<400> SEQUENCE: 67
catatgatac ccggtgtttt gactc                                              25

<210> SEQ ID NO 68
<211> LENGTH: 25
<212> TYPE: DNA
<213> ORGANISM: Artificial
<220> FEATURE:
<223> OTHER INFORMATION: Forward primer

<400> SEQUENCE: 68
catatgatac ccgctgcttt gactc                                              25

<210> SEQ ID NO 69
<211> LENGTH: 25
<212> TYPE: DNA
<213> ORGANISM: Artificial
<220> FEATURE:
<223> OTHER INFORMATION: Forward primer

<400> SEQUENCE: 69
catatgatac ccgctgtttt gactc                                              25

<210> SEQ ID NO 70
<211> LENGTH: 26
<212> TYPE: DNA
<213> ORGANISM: Artificial
<220> FEATURE:
<223> OTHER INFORMATION: Reverse primer

<400> SEQUENCE: 70
gaatatctgg tcatagcatc cgtgaa                                             26

<210> SEQ ID NO 71
<211> LENGTH: 26
<212> TYPE: DNA
<213> ORGANISM: Artificial
<220> FEATURE:
<223> OTHER INFORMATION: Reverse primer

<400> SEQUENCE: 71
gaatatctgg tcatagcttc cgtgaa                                             26

<210> SEQ ID NO 72
<211> LENGTH: 26
<212> TYPE: DNA
<213> ORGANISM: Artificial
<220> FEATURE:
<223> OTHER INFORMATION: Reverse primer

<400> SEQUENCE: 72
gaatatctgg tcatagcgtc cgtgaa                                             26

<210> SEQ ID NO 73
<211> LENGTH: 26
<212> TYPE: DNA
<213> ORGANISM: Artificial
<220> FEATURE:
<223> OTHER INFORMATION: Reverse primer

<400> SEQUENCE: 73
gaatatctgg tcatagcctc cgtgaa                                             26
```